United States Patent
Gumireddy et al.

(10) Patent No.: US 10,745,761 B2
(45) Date of Patent: Aug. 18, 2020

(54) METHOD AND SYSTEMS FOR LUNG CANCER DIAGNOSIS

(71) Applicants: Valley Health System, Paramus, NJ (US); The Wistar Institute, Philadelphia, PA (US)

(72) Inventors: Kiranmai Gumireddy, Bryn Mawr, PA (US); Qihong Huang, Wynnewood, PA (US); Louise C. Showe, Media, PA (US); Ganepola A Ganepola, Hillsdale, NJ (US)

(73) Assignees: Valley Health System, Paramus, NJ (US); The Wistar Institute of Anatomy and Biology, Philadelphia, PA (US)

( * ) Notice: Subject to any disclaimer, the term of this patent is extended or adjusted under 35 U.S.C. 154(b) by 700 days.

(21) Appl. No.: 15/315,808

(22) PCT Filed: Jun. 2, 2015

(86) PCT No.: PCT/US2015/033658
§ 371 (c)(1),
(2) Date: Dec. 2, 2016

(87) PCT Pub. No.: WO2015/187612
PCT Pub. Date: Dec. 10, 2015

(65) Prior Publication Data
US 2019/0177799 A1  Jun. 13, 2019

Related U.S. Application Data

(60) Provisional application No. 62/006,549, filed on Jun. 2, 2014.

(51) Int. Cl.
*C12Q 1/6886* (2018.01)
*G16H 50/30* (2018.01)

(52) U.S. Cl.
CPC ...... *C12Q 1/6886* (2013.01); *C12Q 2600/112* (2013.01); *C12Q 2600/158* (2013.01); *G16H 50/30* (2018.01)

(58) Field of Classification Search
None
See application file for complete search history.

(56) References Cited

U.S. PATENT DOCUMENTS

| | | |
|---|---|---|
| 2006/0068496 A1 | 3/2006 | Kelly |
| 2011/0059856 A1 | 3/2011 | Pison-Rousseaux et al. |
| 2014/0005065 A1 | 1/2014 | Showe et al. |

FOREIGN PATENT DOCUMENTS

| | | |
|---|---|---|
| CN | 105101998 A | 11/2015 |
| WO | 2013182912 A2 | 12/2013 |
| WO | 2014127006 A1 | 8/2014 |

OTHER PUBLICATIONS

Saini et al.; PLos ONE 8(2): e57095, 13 pages (Year: 2013).*
Hu et al. (Reproduction (2009) 137 645-653) (Year: 2009).*
Coleman (Drug Discovery Today. 2003. 8: 233-235).*
Chan (G&P magazine 2006 vol. 6 No. 3 pp. 20-26).*
Radhi (Journal of Clinical Oncology vol. 30 No. 15 Supplement 2012).*
Showe (Cancer Res 2009 vol. 69 No. 24 pp. 9202-9210).*
Max (Clinica Chimica Acta 317 (2002) 39-46).*
Rotunno (Cancer Prey Res 4(10) 1599-1608).*
Saini et al., "A novel cancer testis antigen, A-kinase anchor protein 4 (AKAP4) is a potential biomarker for breast cancer," PLoS One (Feb. 22, 2013); 8(2):1-13, e57095.
Radhi et al., "Novel tumor markers in non-small cell lung cancer detected both in serology and tissue," J Clin Oncol. (Jun. 5, 2012); 30: Abstract e21105.
Chiriva et al., "Identification of new cancer/testis antigens in non-small cell lung cancer," The Journal of Immunology (Apr. 1, 2011); 186, Abstract 165.16.
Gumireddy et al., "AKAP4 is a circulating biomarker for non-smalll cell lung cancer," Oncotarget (Jun. 10, 2015); 6:17637-17647.

* cited by examiner

*Primary Examiner* — Amanda Haney
(74) *Attorney, Agent, or Firm* — Fox Rothschild LLP

(57) ABSTRACT

The present invention relates to methods and systems for high risk screening, diagnosis, prognosis, and surveillance of lung cancer. Accordingly, in one aspect, the invention provides a method for diagnosing or evaluating whether a subject has, or is at risk of having, lung cancer such as NSCLS. The method comprises obtaining a first expression level of the AKAP4 gene of a population of cells from the blood of a test subject; and comparing the first expression level with a first predetermined reference value. A difference between the first expression level and first predetermined reference value correlates with a diagnosis or evaluation of a lung cancer.

14 Claims, 7 Drawing Sheets

Specification includes a Sequence Listing.

Cohort 1

Cohort 2

Combined

Combined set

METHOD AND SYSTEMS FOR LUNG CANCER DIAGNOSIS

CROSS REFERENCE TO RELATED APPLICATION

This application is a U.S. National Phase of International Application No. PCT/US2015/033658, filed Jun. 2, 2015, which claims priority of U.S. Provisional Application No. 62/006,549, filed on Jun. 2, 2014. The contents of the applications are incorporated herein by reference in their entirety.

FIELD OF THE INVENTION

This invention relates to methods and systems for high risk screening, diagnosis, prognosis, and surveillance of lung cancer.

BACKGROUND OF THE INVENTION

Lung cancer, a malignant lung tumor characterized by uncontrolled cell growth in tissues of the lung, is the leading cancer killer in both men and women in the US. More people die from lung cancer than from breast cancer, prostate cancer and colon cancer combined globally. Nevertheless, the five-year survival rate in early stage non-small cell lung cancer (NSCLC) is above 50%. The five-year survival rate drops to below 5% in NSCLC patients with metastatic disease. Although early detection can save lives, screening tests for high-risk individuals are still lacking. Helical low-dose computerized tomography (LDCT) has been used for screening in high-risk populations. However, there are multiple drawbacks associated with LDCT screening including false-negative, false-positive, radiation exposure, and financial cost. Currently no non-invasive test for lung cancer using body fluids such as blood and sputum is available.

In addition, lung nodules are commonly detected on CT. It is reported that up to 51% of smokers 50 years or older have pulmonary nodules on CT. In some cases, it is difficult to differentiate malignant nodules from benign nodules. It is recommended that these undetermined nodules should be followed up with serial CT, which increases substantial radiation exposure to the individuals and financial cost. A blood test for differentiating malignant and benign nodules will be highly beneficial to patients.

Thus, there are urgent needs for blood tests for lung cancer detection and for distinguishing lung cancer from benign lung nodules.

SUMMARY OF INVENTION

This invention relates to methods and systems for high risk screening, diagnosis, prognosis, and surveillance of lung cancer. Accordingly, in one aspect, the invention provides a method for diagnosing or evaluating whether a subject has, or is at risk of having, lung cancer such as NSCLS. The method comprises obtaining a first expression level of the AKAP4 gene of a population of cells from the blood of a test subject; and comparing the first expression level with a first predetermined reference value. A difference between the first expression level and first predetermined reference value correlates with a diagnosis or evaluation of a lung cancer. In one embodiment, the population cells is a population of nucleated cells. For example, the cells can be low-density cells, including peripheral blood mononuclear cells (PBMCs) and associated cells (i.e., PBMC-containing fraction of the blood).

In the method, the first predetermined reference value can be obtained from a control subject selected from the group consisting of the followings: (a) a smoker with malignant disease (e.g., lung cancer), (b) a smoker with non-malignant disease, (c) a former smoker with non-malignant disease, (d) a healthy non-smoker with no disease, (e) a non-smoker who has chronic obstructive pulmonary disease (COPD), (f) a former smoker with COPD, (g) a subject with a solid lung tumor prior to surgery for removal of same, (h) a subject with a solid lung tumor following surgical removal of said tumor, (i) a subject with a solid lung tumor prior to therapy for same, and (j) a subject with a solid lung tumor during or following therapy for same. The control subject (a)-(j) can be the same test subject at a temporally earlier time point. In one embodiment, the test subject is determined to have, or to be at risk of having lung cancer, if the first expression level is above the first predetermined reference value obtained from a control subject that does not have lung cancer.

In some embodiments, the above-described method can further comprise isolating or enriching the nucleated cells or the low-density cells form the blood of the test subject prior to the obtaining step. The obtaining step can include extracting total RNA from the population of the cells, and measuring the level of RNA transcribed from the AKAP4 gene. The measuring step can be conducted by a process comprising PCR, such as RT-PCR, Quantitative-Real Time-Polymerase Chain Reaction (qRT-PCR), nested PCR, or nested qRT-PCR. When nested PCR is conducted, one can use a first pair of primers and a second pair of primers that produce a first amplicon and a second amplicon, respectively. Preferably, the second amplicon is different from the first one, and is included or encompassed within the first one. In one example, the first pair of primers contains the sequences of SEQ IDs: 5 and 6 and the second pair of primers contains the sequences of SEQ IDs: 7 and 8.

Besides the AKAP4 gene, the method can also include detecting or measuring the expression of a second gene selected from the group consisting of (a) hepatitis B virus x associated protein (HBXAP or RSF1), (b) dual-specificity tyrosine-(Y)-phosphorylation regulated kinase 2 (DYRK2), (c) YY1 transcription factor (YY1), (d) chromosome 19 open reading frame 12, transcript variant 1 (C19orf12), (e) thioesterase superfamily member 2 (THEM2), (f) triple functional domain (PTPRF interacting) (TRIO), (g) myeloid-associated differentiation marker, transcript variant 4 (MYADM), (h) BAI1-associated protein 2 (BAIAP2), (i) leucine zipper domain protein (FLJ22386 or ROGDI), (j) DnaJ (Hsp40) homolog, subfamily B, member 14 (DNAJB14), (k) brain and reproductive organ-expressed TNFRSF1A modulator (BRE), (l) transmembrane protein 41A (TMEM41A), (m) chromosome 9 open reading frame 64 (C9orf64), (n) chromosome 20 open reading frame 55, transcript variant 1 (C20orf55 or FAM110A), (o) pecanex-like 2 PCNXL2, (p) RE1-silencing transcription factor (REST), (q) HSPC142 protein (HSPC142 or C19orf62), (r) hypothetical protein BC015148 (LOC93081 or C13orf27), (s) activating signal cointegrator 1 complex subunit 3 (ASCC3), (t) solute carrier family 1, member 5 (SLC1A5), (u) protein tyrosine phosphatase-like A domain containing 1 (PTPLAD1), (v) MRE11meiotic recombination 11 homolog A (MRE11A), (w) hypothetical protein or GTP-binding protein 10 (DKFZP686A10121 or GTPBP10) (y) Soares fetal liver spleen 1NFLS cDNA clone IMAGp998K18127, (z) serpin peptidase inhibitor, clade I (pancpin), member 2 (SERPINI2), (aa) cDNA FLJ44370 fis, clone TRACH3008902 or CAMP responsive element binding protein 1 (CREB1), (bb) coiled-coil domain containing 53 (CCDC53), (cc) ubiquitin specific peptidase 48 (USP48, and (dd) zinc finger and SCAN domain containing 2, transcript variant 3 (ZSCAN2) as described in U.S. Pat. No. 8,476,420, the content of which is incorporated by reference. In that case, the method includes obtaining a second expression level of the second gene and comparing the second expression level of the second gene with a second predetermined reference value in the same manner described above. In one example, the test subject is determined to have, or to be at risk of having lung cancer if both (i) the first expression level is above the first predetermined reference value and (ii) the second expression level is above the second predetermined reference value.

The above method allows one to obtain various diagnoses or evaluations, including one or more of a diagnoses of a lung cancer, a diagnosis of a stage of lung cancer, a diagnosis of a type or classification of a lung cancer, a diagnosis or detection of a recurrence of a lung cancer, a diagnosis or detection of a regression of a lung cancer, a prognosis of a lung cancer, and an evaluation of the response of a lung cancer to a surgical or non-surgical therapy. Accordingly, the test subject can be one who has undergone surgery for solid tumor resection or chemotherapy.

In the above method, the obtaining step can also include contacting the cells, RNAs thereof, or cDNAs produced therefrom with a probe that hybridizes to a RNA or cDNA of the AKAP4 gene or the complement thereof under a stringent condition. The probe can be deposited onto a solid support, e.g., a microarray. Alternatively, to obtain the above-mentioned expression level(s), one can use corresponding antibodies including contacting the cells or a sample therefrom with the antibodies, such as an anti-AKAP4 antibody. One can also sequence RNA or cDNA of AKAP4 to determine AKAP4 level in the sample.

In a second aspect, the invention provides a set of oligonucleotides having a first pair of oligonucleotides or primers that are capable of producing a first amplicon of RNA of the AKAP4 gene; and/or a second pair of oligonucleotides that are capable of producing a second amplicon of said RNA using the first amplicon as a template. The first pair of oligonucleotides can have the sequences of SEQ IDs: 5 and 6; the second pair of oligonucleotides can have the sequences of SEQ IDs: 7 and 8. One skilled in the art can design and use other suitable primers based on the nucleic acid sequences described below.

Also provided is a kit containing the set of oligonucleotides and packaging material therefor. In preferred embodiments, the kit can further contain one or more reagents elected from the group consisting of a buffer, a DNA polymerase, an RNAse inhibitor, extension nucleotides, random primers, and a probe.

The details of one or more embodiments of the invention are set forth in the description below. Other features, objectives, and advantages of the invention will be apparent from the description and from the claims.

BRIEF DESCRIPTION OF THE DRAWINGS

FIG. 2 illustrates that unbiased nested PCR screening of 130 CTAs identifies AKAP4 and GAGE4 as potential candidates for NSCLC diagnosis based on a small discovery set of samples.

FIG. 3 illustrates that AKAP4 serves as a circulating biomarker for NSCLC in two cohorts of NSCLC patients and controls.

FIG. 4 illustrates that AKAP4 is a blood based biomarker for NSCLC early detection. FIG. 4B illustrates the distinction between malignant and benign lung nodules.

DETAILED DESCRIPTION OF THE INVENTION

Figure 1:
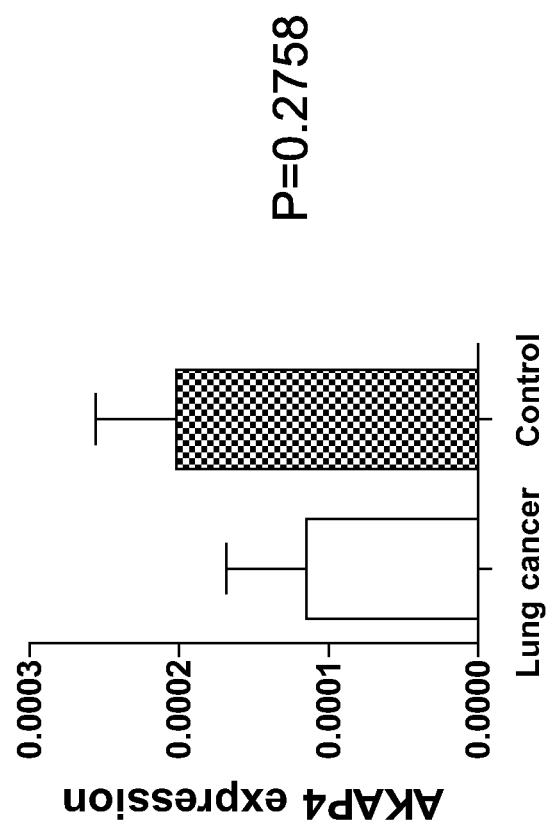
FIG. 1 is a diagram showing that AKAP4 expression in the whole blood cell samples from NSCLC and control and that there is no significant difference between NSCLC and control in whole blood samples.

This invention is based, at least in part, on unexpected discoveries that the expression of the AKAP4 gene in a population of nucleated or low-density cells from the blood of a subject is highly correlated with lung cancer even at very early stage of the disorder and its recurrence after a therapy. As disclosed herein, the AKAP4 gene and related methods and reagents of this invention can be used in a non-invasive test for early detection of early stage lung cancer. The test can also be used for differentiating malignant lung nodules from benign nodules, which are commonly seen on CT scans. Inventors' studies on longitudinal samples also shown that this test can be used as a predictive biomarker to identify responders and non-responders in treatment and disease recurrence.

Biomarkers

As disclosed herein, the AKAP4 gene was identified as a peripheral blood marker based on its altered expression patterns in a population of cells from the blood of lung cancer patients and healthy subjects. Listed below are the nucleic acid and polypeptide sequences of two isoforms of human AKAP4.

NM_003886

(SEQ ID NO: 1)

```
   1    ccagctggca gtcaaggctg taggagggca tggagagttg aagaaaaaag cagtatcttg
  61    aggcagactg gaagagtcat cacagcatcc aaatcaacaa gaaaacatca ttccagggtc
 121    ctacatgatg gcgtactctg atactacaat gatgtctgat gatattgact ggttacgcag
 181    ccacagggt gtgtgcaagg tagatctcta caacccagaa ggacagcaag atcaggaccg
 241    gaaagtgata tgctttgtcg atgtgtccac cctgaatgta gaagataaag attacaagga
 301    tgctgctagt tccagctcag aaggcaactt aaacctggga agtctggaag aaaaagagat
 361    tatcgtgatc aaggacactg agaagaaaga ccagtctaag acagagggat ctgtatgcct
 421    tttcaaacaa gctccctctg atcctgtaag tgtcctcaac tggcttctca gtgatctcca
 481    gaagtatgcc ttgggtttcc aacatgcact gagcccctca acctctacct gtaaacataa
 541    agtaggagac acagagggcg aaatatcacag agcatcctct gagaactgct acagtgtcta
 601    tgccgatcaa gtgaacatag attatttgat gaacagacct caaaacctac gtctagaaat
 661    gacagcagct aaaaacacca acaataatca aagtccttca gctcctccag ccaaacctcc
 721    tagcactcag agagcagtca tttcccctga tggagaatgt tctatagatg acctttcctt
 781    ctacgtcaac cgactatctt ctctggtaat ccagatggcc cataaggaaa tcaaggagaa
 841    gttggaaggt aaaagcaaat gccttcatca ttcaatctgt ccatcccctg ggaacaaaga
 901    gagaatcagt ccccgaactc ctgcgagcaa gattgcttct gaaatggcct atgaagctgt
 961    ggaactgaca gctgcagaaa tgcgtggcac tggagaggag tccagggaag gtggccagaa
1021    aagctttcta tatagcgaat tatccaacaa gagcaaaagt ggagacaaac agatgtccca
1081    gagagagagc aaagaatttg cagattccat cagcaagggg ctcatggttt atgcaaatca
1141    ggtggcatct gacatgatgg tctctctcat gaagaccttg aaagtgcaca gctctgggaa
1201    gccaattcca gcatctgtgg tcctgaagag ggtgttgcta aggcacacca aggagattgt
1261    gtccgatttg attgattctt gcatgaagaa cctgcataat attactgggg tcctgatgac
1321    tgactcagac tttgtctcag ctgtcaagag aaatctgttc aaccagtgga aacaaaatgc
1381    tacagacatc atggaggcca tgctgaagcg cttggtcagt gcccttatag gtgaggagaa
1441    ggagactaag tctcagagtc tgtcatatgc atctttaaaa gctgggtccc atgatcccaa
1501    atgcaggaat cagagtcttg aattctccac catgaaagct gaaatgaaag agagggacaa
1561    aggcaaaatg aaatcagacc catgcaagtc actgactagt gctgagaaag tcggtgaaca
1621    cattctcaaa gagggcctaa ccatctggaa ccaaaagcaa ggaaactcat gcaaggtggc
1681    taccaaagca tgcagcaata aagatgagaa aggagaaaag atcaatgctt ccacagattc
```

-continued

```
1741  actggccaag gacctgattg tctctgccct taagctgatc cagtaccatc tgacccagca
1801  gactaagggc aaagatacat gtgaagaaga ctgtcctggt tccaccatgg gctatatggc
1861  tcagagtact caatatgaaa agtgtggagg tggccaaagt gccaaagcac tttcagtgaa
1921  acaactagaa tctcacagag cccctggacc atccacctgt caaaaggaga ccaacacct
1981  ggactcccag aaaatggata tgtcaaacat cgttctaatg ctgattcaga aactgcttaa
2041  tgagaacccc ttcaaatgtg aggatccatg cgaaggtgag aacaagtgtt ctgagcccag
2101  ggcaagcaaa gcagcttcca tgtccaacag atctgacaaa gcggaagaac aatgccagga
2161  gcatcaagaa cttgactgta ccagtgggat gaagcaagcg aacgggcaat ttatagataa
2221  actagtagaa tctgtgatga agctctgcct tatcatggct aagtatagca acgatggggc
2281  agcccttgct gagttggaag aacaagcagc ctcggcaaat aagcccaatt tcaggggcac
2341  cagatgcatt cacagtggtg caatgccaca gaactatcaa gactctcttg gacatgaagt
2401  aattgtcaat aatcagtgct ctacaaatag cttgcagaag cagctccagg ctgtcctgca
2461  gtggattgca gcctcccagt ttaacgtgcc catgctctac ttcatgggag ataaggatgg
2521  acaactggaa aagcttcctc aggtttcagc taaagcagca gagaagggg acagtgtagg
2581  aggtcttctt caagaggtca tgaagtttgc caaggaacgg caaccagatg aagctgtggg
2641  aaaggtggcc aggaaacagt tgctggactg gctgctcgct aacctgtgag ctgatccttg
2701  actcctcttc atcttagccc ccctagcagc attccatccc agccagagca ccccaccat
2761  caggccagtc aactgcacaa tacacaactg tatttcccaa tacacttgag cagttgcctg
2821  tgaatgtaag aggtgtcaac aaactgggaa ataaaataaa aaaaataat aataaatgtg
2881  t
```

NP_003877
(SEQ ID NO: 2)

MMAYSDTIMMSDDIDWLRSHRGVCKVDLYNPEGQQDQDRKVICFVDVSTLNVEDKDYKDAASSSSEGNLNLGSLEEKE
IIVIKDTEKKDQSKTEGSVCLFKQAPSDPVSVLNWLLSDLQKYALGFQHALSPSTSICKHKVGDTEGEYHRASSENCY
SVYADQVNIDYLMNRPQNLRLEMTAAKNINNNQSPSAPPAKPPSTQRAVISPDGECSIDDLSFYVNRLSSLVIQMAHK
EIKEKLEGKSKCLHHSICPSPGNKERISPRIPASKIASEMAYEAVELTAAEMRGIGEESREGGQKSFLYSELSNKSKS
GDKQMSQRESKEFADSISKGLMVYANQVASDMMVSLMKTLKVHSSGKPIPASVVLKRVLLRHTKEIVSDLIDSCMKNL
HNITGVLMTDSDFVSAVKRNLFNQWKQNATDIMEAMLKRLVSALIGEEKETKSQSLSYASLKAGSHDPKCRNQSLEFS
TMKAEMKERDKGKMKSDPCKSLTSAEKVGEHILKEGLTIWNQKQGNSCKVATKACSNKDEKGEKINASTDSLAKDLIV
SALKLIQYHLTQQTKGKDTCEEDCPGSTMGYMAQSTQYEKCGGGQSAKALSVKQLESHRAPGPSTCQKENQHLDSQKM
DMSNIVLMLIQKLLNENPFKCEDPCEGENKCSEPRASKAASMSNRSDKAEEQCQEHQELDCTSGMKQANGQFIDKLVE
SVMKLCLIMAKYSNDGAALAELEEQAASANKPNFRGTRCIHSGAMPQNYQDSLGHEVIVNNQCSTNSLQKQLQAVLQW
IAASQFNVPMLYFMGDKDGQLEKLPQVSAKAAEKGYSVGGLLQEVMKFAKERQPDEAVGKVARKQLLDWLLANL

NM_139289
(SEQ ID NO: 3)

```
  1   caggggtggc agccaactgc aggtgcccaa gaacttggca cttctcagtt ccatctaaag
 61   gggcacatct cccttctggg tgtcacgttt tcagccaaac atctaaaaga acttcatcat
121   caagatgtct gatgatattg actggttacg cagccacagg ggtgtgtgca aggtagatct
181   ctacaaccca gaaggacagc aagatcagga ccggaaagtg atatgctttg tcgatgtgtc
241   caccctgaat gtagaagata agattacaa ggatgctgct agttccagct cagaaggcaa
301   cttaaacctg ggaagtctgg aagaaaaaga gattatcgtg atcaaggaca ctgagaagaa
361   agaccagtct aagacagagg gatctgtatg ccttttcaaa caagctccct ctgatcctgt
```

-continued

```
 421   aagtgtcctc aactggcttc tcagtgatct ccagaagtat gccttgggtt tccaacatgc
 481   actgagcccc tcaacctcta cctgtaaaca taaagtagga cacacagagg gcgaatatca
 541   cagagcatcc tctgagaact gctacagtgt ctatgccgat caagtgaaca tagattattt
 601   gatgaacaga cctcaaaacc tacgtctaga aatgacagca gctaaaaaca ccaacaataa
 661   tcaaagtcct tcagctcctc cagccaaacc tcctagcact cagagagcag tcatttcccc
 721   tgatggagaa tgttctatag atgacctttc cttctacgtc aaccgactat cttctctggt
 781   aatccagatg gcccataagg aaatcaagga gaagttggaa ggtaaaagca aatgccttca
 841   tcattcaatc tgtccatccc ctgggaacaa agagagaatc agtccccgaa ctcctgcgag
 901   caagattgct tctgaaatgg cctatgaagc tgtggaactg acagctgcag aaatgcgtgg
 961   cactggagag gagtccaggg aaggtggcca gaaaagcttt ctatatagcg aattatccaa
1021   caagagcaaa agtggagaca acagatgtc ccagagagag agcaaagaat ttgcagattc
1081   catcagcaag gggctcatgg tttatgcaaa tcaggtggca tctgacatga tggtctctct
1141   catgaagacc ttgaaagtgc acagctctgg gaagccaatt ccagcatctg tggtcctgaa
1201   gagggtgttg ctaaggcaca ccaaggagat tgtgtccgat ttgattgatt cttgcatgaa
1261   gaacctgcat aatattactg gggtcctgat gactgactca gactttgtct cagctgtcaa
1321   gagaaatctg ttcaaccagt ggaaacaaaa tgctacagac atcatggagg ccatgctgaa
1381   gcgcttggtc agtgcccctta taggtgagga aaggagact aagtctcaga gtctgtcata
1441   tgcatcttta aaagctgggt cccatgatcc caaatgcagg aatcagagtc ttgaattctc
1501   caccatgaaa gctgaaatga agagaggga caaaggcaaa atgaaatcag acccatgcaa
1561   gtcactgact agtgctgaga agtcggtga acacattctc aaagagggcc taaccatctg
1621   gaaccaaaag caaggaaact catgcaaggt ggctaccaaa gcatgcagca ataaagatga
1681   gaaaggagaa aagatcaatg cttccacaga ttcactggcc aaggacctga ttgtctctgc
1741   ccttaagctg atccagtacc atctgaccca gcagactaag ggcaaagata catgtgaaga
1801   agactgtcct ggttccacca tgggctatat ggctcagagt actcaatatg aaaagtgtgg
1861   aggtggccaa agtgccaaag cactttcagt gaaacaacta gaatctcaca gagcccctgg
1921   accatccacc tgtcaaaagg agaaccaaca cctggactcc cagaaaatgg atatgtcaaa
1981   catcgttcta atgctgattc agaaactgct taatgagaac cccttcaaat gtgaggatcc
2041   atgcgaaggt gagaacaagt gttctgagcc cagggcaagc aaagcagctt ccatgtccaa
2101   cagatctgac aaagcggaag aacaatgcca ggagcatcaa gaacttgact gtaccagtgg
2161   gatgaagcaa gcgaacgggc aatttataga taaactagta gaatctgtga tgaagctctg
2221   ccttatcatg gctaagtata gcaacgatgg ggcagccctt gctgagttgg aagaacaagc
2281   agcctcggca aataagccca atttcagggg caccagatgc attcacagtg gtgcaatgcc
2341   acagaactat caagactctc ttggacatga agtaattgtc aataatcagt gctctacaaa
2401   tagcttgcag aagcagctcc aggctgtcct gcagtggatt gcagcctccc agtttaacgt
2461   gcccatgctc tacttcatgg gagataagga tggacaactg gaaaagcttc ctcaggtttc
2521   agctaaagca gcagagaagg ggtacagtgt aggaggtctt cttcaagagg tcatgaagtt
2581   tgccaaggaa cggcaaccag atgaagctgt gggaaaggtg gccaggaaac agttgctgga
2641   ctggctgctc gctaacctgt gagctgatcc ttgactcctc ttcatcttag cccccctagc
2701   agcattccat cccagccaga gcaccccac catcaggcca gtcaactgca caatacacaa
```

```
                           -continued
2761     ctgtatttcc caatacactt gagcagttgc ctgtgaatgt aagaggtgtc aacaaactgg 2821     gaaataaaat aaaaaaaaat aataaaaaaa aaaaaaaaaa aaaaaaa NP_647450
                                                                    (SEQ ID NO: 4)
MSDDIDWLRSHRGVCKVDLYNPEGQQDQDRKVICFVDVSTLNVEDKDYKDAASSSSEGNLNLGSLEEKEIIVIKDTEK

KDQSKTEGSVCLFKQAPSDPVSVLNWLLSDLQKYALGFQHALSPSTSTCKHKVGDTEGEYHRASSENCYSVYADQVNI

DYLMNRPQNLRLEMTAAKNTNNNQSPSAPPAKPPSTQRAVISPDGECSIDDLSFYVNRLSSLVIQMAHKEIKEKLEGK

SKCLHHSICPSPGNKERISPRTPASKIASEMAYEAVELTAAEMRGTGEESREGGQKSFLYSELSNKSKSGDKQMSQRE

SKEFADSISKGLMVYANQVASDMMVSLMKTLKVHSSGKPIPASVVLKRVLLRHTKEIVSDLIDSCMKNLHNITGVLMT

DSDFVSAVKRNLFNQWKQNATDIMEAMLKRLVSALIGEEKETKSQSLSYASLKAGSHDPKCRNQSLEFSTMKAEMKER

DKGKMKSDPCKSLTSAEKVGEHILKEGLTIWNQKQGNSCKVATKACSNKDEKGEKINASTDSLAKDLIVSALKLIQYH

LTQQTKGKDTCEEDCPGSTMGYMAQSTQYEKCGGGQSAKALSVKQLESHRAPGPSTCQKENQHLDSQKMDMSNIVLML

IQKLLNENPFKCEDPCEGENKCSEPRASKAASMSNRSDKAEEQCQEHQELDCTSGMKQANGQFIDKLVESVMKLCLIM

AKYSNDGAALAELEEQAASANKPNFRGTRCIHSGAMPQNYQDSLGHEVIVNNQCSTNSLQKQLQAVLQWIAASQFNVP

MLYFMGDKDGQLEKLPQVSAKAAEKGYSVGGLLQEVMKFAKERQPDEAVGKVARKQLLDWLLANL
```

The above-mentioned discovery was surprising and unexpected as efforts had been made to identify gene expression profiles in peripheral blood mononuclear cells that can distinguish patients with non-small cell lung cancer from patients with nonmalignant lung disease. For example, Showe et al. Cancer Res. 2009 Dec. 15; 69(24):9202-10 and U.S. Pat. No. 8,476,420 describe a 29-gene signature that separates these two classes. Yet, the AKAP4 gene was not one of the 29 genes.

In addition, as disclosed herein, the specificity and sensitivity of tests based on AKAP4 gene expression in low-density cells or PBMC-containing fraction from the blood are superior to known lung cancer detection methods using body fluids including plasma, sputum, serum, or PBMC. In fact, the results shown in the examples below (including the AUC of ROC curve analysis) are far better than conventional methods based on other peripheral blood markers. In addition, the studies disclosed here used a sample size larger than others, indicating application of AKAP4 gene expression in early detection of lung cancer, differentiation of malignant and benign lung nodules, and lung cancer recurrence detection. The AKAP4 gene expression can be used alone or used in combination with other known markers for lung cancers. Examples of such known markers include those described in Showe et al. Cancer Res. 2009 Dec. 15; 69(24):9202-10 and U.S. Pat. No. 8,476,420, both of which are incorporated by reference in their entireties.

The advantage of the invention disclosed herein for early lung cancer detection is significant. The 5-year survival rate is 50-70% in lung cancer patients whose cancers are detected at early stage and can be treated. The 5-year survival rate is below 5% in patients with metastatic disease. Currently only 15% of lung cancer patients are diagnosed at early stage. The invention disclosed herein allows one to detect lung cancer at a very early stage and thereby significantly improve lung cancer patients' survival and reduce lung cancer death.

Diagnosis and Prognosis Methods

The markers, related kits, reagents and systems disclosed herein can be used in determining whether a subject has, or is at risk of having, a lung cancer. Alternatively, they can be used for determining a prognosis of such a disorder in a subject.

Diagnosis Methods

In one aspect, the invention provides qualitative and quantitative information to determine whether a subject has or is predisposed to lung cancer. A subject having lung cancer or prone to it can be determined based on the expression levels, patterns, or profiles of the above-described genes or their expression products (RNAs or polypeptides) in a test sample from the subject. In other words, the products can be used as markers to indicate the presence or absence of the disorder. Diagnostic and prognostic assays of the invention include methods for assessing the expression level of the products. The methods and kits allow one to detect lung cancer. For example, a relative increase in the expression level of AKAP4 gene in PBMC-containing fraction from the blood is indicative of presence the disorder. Conversely, a lower expression level or a lack of the expression is indicative lack of the disorder.

The presence, level, or absence of the expression products in a test sample can be evaluated by obtaining a test sample from a test subject and contacting the test sample with a compound or an agent capable of detecting the nucleic acid (e.g., RNA or DNA probe). The test sample includes tissues, cells and biological fluids isolated from a subject, as well as tissues, cells and fluids present within a subject. The level of expression of a gene(s) of interest can be measured in a number of ways, including measuring the RNA encoded by the gene.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, Wis.), and 7.5 kb Poly(A)-Tailed RNA from LIFE TECHNOLOGIES (Rockville, Md.). Lysates may be used immediately or stored frozen at, e.g., −80° C.

Optionally, total RNA can be purified from cell lysates (or other types of samples) using silica-based isolation in an automation-compatible, 96-well format, such as the RNEASY purification platform (QIAGEN, Inc., Valencia, Calif.). Other RNA isolation methods are contemplated, such as extraction with silica-coated beads or guanidinium. Further methods for RNA isolation and preparation can be devised by one skilled in the art.

The methods of the present invention can be performed using crude samples (e.g., blood, serum, plasma, or cell lysates). RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products.

The level of RNA corresponding to a gene in a cell can be determined both in situ and in vitro. RNA isolated from a test sample or cDNA prepared from it can be used in sequencing, hybridization or amplification assays that include, Southern or Northern analyses, PCR analyses, and probe arrays. An exemplary diagnostic method for the detection of RNA levels involves contacting the isolated RNA or cDNA or cRNA with a nucleic acid probe that can hybridize to the RNA encoded by the gene. The probe can be a full-length nucleic acid or a portion thereof, such as an oligonucleotide of at least 10 nucleotides in length and sufficient to specifically hybridize under stringent conditions to the RNA.

In one format, RNA (or cDNA prepared from it) is immobilized on a surface and contacted with the probes, for example, by running the isolated RNA on an agarose gel and transferring the RNA from the gel to a membrane, such as nitrocellulose. In another format, the probes are immobilized on a surface and the RNA (or cDNA or cRNA) is contacted with the probes, for example, in a gene chip array. A skilled artisan can adapt known RNA detection methods for detecting the level of RNA (or cDNA or cRNA prepared from it).

The level of RNA (or cDNA prepared from it) in a sample encoded by a gene to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art.

In another embodiment, the methods of the invention further include contacting a control sample with a compound or agent capable of detecting the RNA of a gene and comparing the presence of the RNA in the control sample with the presence of the RNA in the test sample.

The above-described methods and markers can be used to assess the risk of a subject for developing lung cancer. In particular, the invention can be applied to those in high risk cohort who already have certain risks so as to gain critical insight into early detection.

A change in levels of gene products associated with lung cancer can be detected prior to, or in the early stages of, the development of transformed or neoplastic phenotypes in cells of a subject. The invention therefore also provides a method for screening a subject who is at risk of developing lung cancer, comprising evaluating the level of the AKAP4 gene expression in PBMC-containing fraction of the blood, and optionally the levels of one or more of other markers mentioned above in a biological sample obtained from the subject. Accordingly, a difference or alteration of the level of the gene product, or combination of gene products, in the biological sample as compared to the level of a corresponding gene product in a control sample, is indicative of the subject being at risk for developing lung cancer. The biological sample used for such screening can include a population of cells from the blood of the subject that is either normal or suspected to be precancerous. Subjects with a change in the level of one or more gene products associated with lung cancer are candidates for further monitoring and testing. Such further testing can comprise histological examination of tissue samples, CT, or other techniques within the skill in the art.

By "diagnosis" or "evaluation" refers to a diagnosis of a lung cancer, a diagnosis of a stage of lung cancer, a diagnosis of a type or classification of a lung cancer, a diagnosis or detection of a recurrence of a lung cancer, a diagnosis or detection of a regression of a lung cancer, a prognosis of a lung cancer, or an evaluation of the response of a lung cancer to a surgical or non-surgical therapy.

Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., lung cancer.

Prognosis Methods

The diagnostic methods described above can identify subjects having, or at risk of developing, lung cancer. In addition, changes in expression levels and/or trends of the above-mentioned genes (or a subset of it) in a biological sample, e.g., a PBMC-containing fraction of the blood, can provide an early indication of recovery or lack thereof. For example, a further increase (or decline) or persistently-altered gene expression levels of the AKAP4 gene indicate a poor prognosis, i.e., lack of improvement or health decline. Accordingly, these genes allow one to assess post-treatment recovery of cancer. The analysis of this select group of genes or a subset thereof indicates outcomes of the conditions.

The prognostic assays described herein can be used to determine whether a subject is suitable to be administered with an agent (e.g., an agonist, antagonist, peptidomimetic, protein, peptide, nucleic acid, small molecule, or other drug candidate) to treat lung cancer. For example, such assays can be used to determine whether a subject can be administered with a chemotherapeutic agent.

Thus, also provided by this invention is a method of monitoring a treatment for lung cancer in a subject. For this purpose, gene expression levels of the genes disclosed herein, e.g., AKAP4, can be determined for test samples from a subject before, during, or after undergoing a treatment. The magnitudes of the changes in the levels as compared to a baseline level are then assessed. A decrease of the magnitudes of the changes after the treatment indicates that the subject can be further treated by the same treatment. For example, a relative decrease in the expression level of one or more up-regulated genes, e.g., AKAP4, is indicative of recovery from the disorder. Conversely, further increase or persistent high expression levels of one or more of the up-regulated genes is indicate lack of improvement or health decline.

Information obtained from practice of the above assays is useful in prognostication, identifying progression of, and clinical management of diseases and other deleterious conditions affecting an individual subject's health status. In preferred embodiments, the foregoing diagnostic assays provide information useful in prognostication, identifying progression of and management of lung cancer. The information more specifically assists the clinician in designing chemotherapeutic or other treatment regimens to eradicate such conditions from the body of an afflicted subject, a human.

The term "prognosis" as used herein refers to the prediction of the probable course and outcome of a clinical condition or disease, such as the likelihood of cancer-attributable death or progression, including recurrence, metastatic spread, and drug resistance, of a neoplastic disease, such as lung cancer. A prognosis is usually made by evaluating factors or symptoms of a disease that are indicative of a favorable or unfavorable course or outcome of the disease.

The term "prediction" is used herein to refer to the likelihood that a patient will respond either favorably or unfavorably to a drug or set of drugs, and also the extent of those responses, or that a patient will survive, following surgical removal of the primary tumor and/or chemotherapy for a certain period of time without cancer recurrence. The predictive methods of the present invention can be used clinically to make treatment decisions by choosing the most appropriate treatment modalities for any particular patient. The predictive methods described herein are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

Detecting AKAP4 in Peripheral Blood

AKAP4 is a member of the A-kinase anchor proteins which bind the Protein kinase A (PKA) regulatory subunit and functions to anchor PKA to specific cellular locations. AKAP4 is a known cancer/testis gene located on the X chromosome and has been shown to be aberrantly expressed in a variety of different cancers (Agarwal S, et al. *Journal of the International Gynecological Cancer Society* 2013; 23(4):650-8; Agarwal S, et al. *Oncoimmunology* 2013; 2(5): e24270; and Chiriva-Internati M, et al. *Chest* 2014) as well as on circulating tumor cells (CTCs) (Chiriva-Internati M, et al. *Chest* 2014). It has been identified as a tumor antigen, and as a potential therapeutic target for cervical and ovarian cancer (Agarwal S, et al. *Journal of the International Gynecological Cancer Society* 2013; 23(4):650-8; Agarwal S, et al. *Oncoimmunology* 2013; 2(5):e24270), multiple myeloma (Mirandola L, et al. *Cancer* 2011; 11:394), breast cancer (Saini S, et al. PLoS One 2013; 8(2):e57095), prostate cancers (Chiriva-Internati M, et al. *Prostate* 2012; 72(1):12-23) and importantly for NSCLCs (Chiriva-Internati M, et al. *Chest* 2014). Because expression of AKAP4 is normally confined to testis (Hofmann O, et al. *Proc Natl Acad Sci USA* 2008; 105(51):20422-7) the background expression in cancer free controls is essentially negative. While the detection of this message in PBMC samples raises the possibility expression is associated with CTCs, CTC numbers, especially in our early stage samples are expected to be quite low. Another potential source of the AKAP4 signal are tumor derived exosomes which are released in large numbers and engulfed by tumor infiltrating lymphocytes including macrophages that are included in the PBMC fraction (Iero M, et al. *Cell Death Differ* 2007; 15(1):80-88; Yang C, et al. *Clinical and Developmental Immunology* 2011; 2011:11; Burke M, et al. *Journal of Proteome Research* 2013; 13(2):836-43; and Clayton A, et al. *Cancer Research* 2007; 67(15):7458-66. A third alternative that low level expression is induced in specific immune cells in the PBMC fraction by the presence of a tumor in the lung cannot be eliminated, but seems less likely.

The above-described methods involve detecting the AKAP4 gene expression in a PBMC-containing fraction of the blood. As disclosed herein, the human AKAP4 gene normally does not express in peripheral blood cells. Even in cancer patients, the level of AKAP4 gene expression in peripheral blood is extremely low. To detect or assess the AKAP4 gene expression level, it is preferred to enrich or isolate a population of low-density cells which include mononucleated cells or mononuclear cells from the blood to obtain a PBMC-containing fraction of the blood before assaying. Indeed, as shown in the examples below, when the whole blood was used, AKAP4 expression did not allow one to differentiate lung cancer from control.

As used herein "low-density cells" refers to cells from the blood that have a density lower than that of granulocytes or red blood cells and higher than the plasma so that in a Ficoll density gradient separation (such as BD Vacutainer® CPT™ Cell Preparation Tube described below) they are in a layer above the granulocytes or red blood cell layer and the Ficoll (or density gradient liquid) layer and below the plasma layer. In other words, the low-density cells co-migrate with and include the PBMCs. Examples of low-density cells include mononuclear cells of PBMCs (including lymphocytes, monocytes, and dendritic cells) and other cells co-purified with PBMCs using methods for isolating PBMCs from the blood. Accordingly, the population of low-density cells is also called PBMC-containing fraction of the blood. As used herein "mononucleated cell" or "mononuclear cell" refers to a cell that is present in the peripheral blood and has a single round nucleus. These cells can be extracted from whole blood in the manner described in the example section below. For example, they can be isolated or enriched using ficoll, a hydrophilic polysaccharide, which separates the blood into a top layer of plasma, followed by a layer of PBMC-containing fraction and a bottom fraction of polymorphonuclear cells (such as neutrophils and eosinophils) and erythrocytes. A cell fraction containing the low-density cells can be obtained using several methods for isolating or enriching PBMCs. An exemplary protocol for obtaining such PBMC-containing cell fraction, using the BD Vacutainer® CPT™ Cell Preparation Tube. is provided below:

1. 6-8 mls of blood is collected either in a CPT vacutainer tube or as anti-coagulated blood samples for Ficoll Hypagque gradient and proceed as follows 2. Centrifuge samples at room temp (18-25° C.) in a horizontal rotor (Swing out head) for 30 minutes at 3130 RPM—on Sorval Centrifuge in Tissue Culture Rm—Brake OFF—Flat below).

3. After centrifugation, mononuclear cells and platelets will be in a whitish layer ($2^{nd}$ layer) just under the plasma layer (top layer). Aspirate off the plasma top layer into some bleach without disturbing the mononuclear cell layer.

4. Collect the mononuclear cell layer with a 1 ml or 5 ml pipette and eject slowly into new tube 15 ml conical tube.

5. Pour PBS to fill up 15 ml blue tube and invert tube. (This is the first wash step to reduce the quantity of platelets present in the PBMC layer).

6. Centrifuge for 15 minutes at room temp at 1335 RPM—on Sorval Centrifuge in Tissue Culture Rm) (BRAKE ON).

7. Aspirate as much supernatant as possible without disturbing pellet—leave about 1 ml of supernatant with pellet for resuspension. Tap the tube with finger to resuspend the pellet in the 1 ml of supernatant.

8. Add PBS to bring volume up again in 15 ml tube. Mix by inverting tube. (This is the second wash step to reduce the quantity of platelets present in the PBMC layer).

9. Centrifuge for 15 minutes at room temp at 1335 RPM—on Sorval Centrifuge in Tissue Culture Rm) (BRAKE ON).

10. Aspirate all supernatant without disturbing pellet. Discard supernatant into some bleach. Put tube containing the pellet upside down and let sit at room temp for 2 minutes to drain off all supernatant.

Once the PBMC-containing cell fraction is obtained, the AKAP4 gene expression can be measured using PCR. Since the level of AKAP4 gene expression in peripheral blood is extremely low, conventional PCR may not be sensitive enough to detect it. Accordingly, more sensitive approaches should be used. For example, methods with two or more rounds of PCRs, such as nested PCR, can be used. As showed in the examples below, quantitative nested RT-PCR was successfully used to determine the expression of AKAP4 in blood (or PBMC) and showed that the biomarker is able to detect early stage of lung cancer and recurrence, and differentiate malignant and benign lung nodules.

Presence and/or expression level/amount of AKAP4 in a sample can also be analyzed by a number of methodologies, many of which are known in the art and understood by the skilled artisan, including, but not limited to, immunohistochemical ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), Taqman probes, RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments, presence and/or expression level/amount of AKAP4 is determined using a method comprising: (a) performing gene expression profiling, PCR (such as rtPCR), Taqman probes, RNA-seq, microarray analysis, SAGE, MassARRAY technique, or FISH on a sample (such as a subject cancer sample); and (b) determining presence and/or expression level/amount of a biomarker in the sample. In some embodiments, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. In one embodiment, the PCR method is qRT-PCR. In one embodiment, the PCR method is multiplex-PCR. In some embodiments, gene expression is measured by microarray. In some embodiments, gene expression is measured by qRT-PCR. In some embodiments, expression is measured by multiplex-PCR.

Accurate quantification of the copy of RNA molecules of this biomarker is needed for clinical applications. Thus, in one embodiment, digital PCR can be used in this invention to quantify the RNA copies of this biomarker. Currently there are a number of digital PCR platforms available including those by Fluidigm, Life Technologies, Bio-Rad and RainDance. In one example, one can use the Bio-Rad ddPCR system for digital PCR assay development because of its number of partition per run, multiplex capability and cost. This system has over 1.3 million partitions per run, more than the 36,960 and 3,072 partitions of the Fluidigm and Life Technologies systems respectively. Although it has less partitions than the RainDance system, which has up to 80 million partitions, the accuracy of RNA copies will not be different significantly because of the abundance of the AKAP4 biomarker, whereas the cost is 70-90% lower than the RainDance system per run.

One can use the blood RNA samples from lung cancer patients and healthy controls as disclosed herein. To that end, he or she can optimize the quantity of the RNA used for digital PCR by using, e.g., EvaGreen and probe-based digital PCR systems. The expression level of the AKAP4 biomarker can be determined using digital PCR and analyzing the ROC curves of (1) all NSCLC vs healthy control; (2) stage I NSCLC vs healthy control; and (3) all NSCLC vs benign nodule. After that, one can compare the digital PCR results with the quantitative RT-PCR results and determine a cut-off reference value of this biomarker for sample analysis. The same strategy can also be used in longitudinal samples to accurately detect disease recurrence.

Digital PCR of the AKAP4 biomarker can also be used in additional lung cancer and healthy control patients. For example, blood samples can be collected from 300 NSCLC lung cancer patients and 300 healthy controls. Among 300 healthy controls, at least 100 are individuals with benign lung nodules either confirmed by serial CT or biopsy. Longitudinal blood samples are also collected from lung cancer patients who underwent treatment, are in remission, and are followed up periodically. RNAs from these samples are isolated and digital PCR then is carried out to determine the expression level of the biomarker for early detection of lung cancer and recurrence; and differentiate malignant and benign nodules.

Although PCR-based methods are preferred, immunocytochemistry methods are also suitable for detecting the expression levels of the gene expression products described for use in the methods and systems of this invention. Antibodies or antisera, preferably monoclonal antibodies, or other protein-binding ligands specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Protocols and kits for immunohistochemical analyses are well known in the art and are commercially available.

Anti-AKAP4 antibody can be detected in patients suffering with lung cancer using a variety of methods known in the art, including by way of example ELISA assays. In one example, recombinant AKAP4 purified protein at the concentration of 4 µg/ml in coating buffer (15 mmol/L $Na_2CO_3$, 35 mmol/L $NaHCO_3$, pH 9.4) is coated in 96-well plates (Nunc, Roskilde, Denmark) overnight at 4° C. Non-specific sites are blocked with 3% non-fat skimmed milk for 1 h at room temperature and incubated with lung cancer patients or healthy normal's sera in blocking solution for 2 h at room temperature. Plates are washed with PBS containing 0.5% Tween 20 (PBST) and incubated with horsereddish-peroxidase conjugated anti-human IgG (Jackson Immunoresearch Laboratories, West Grove, Pa.) for 1 h at room temperature. Absorbance is observed colorimetrically at 492 nm by using o-Phenylenediamine dihydrochloride as a substrate. All lung cancer patients and healthy donor samples are tested in duplicates and mean is used for analysis. The inter-assay and intra-assay coefficients of variation are calculated from three independent experiments.

Other methods suitable for detecting gene expression levels are known in the art. See e.g., U.S. Pat. No. 7,081,340. Such methods of gene expression detecting/profiling include methods based on hybridization analysis of polynucleotides, methods based on sequencing of polynucleotides, and proteomics-based methods. The most commonly used methods known in the art for the quantification of mRNA expression in a sample include northern blotting, in situ hybridization, and RNAse protection assays. Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), gene expression analysis by massively parallel signature sequencing (MPSS), and Next Generation Sequencing.

Arrays

Also provided in the invention is a biochip or array. The biochip/array may contain a solid or semi-solid substrate having an attached probe or plurality of probes that are capable of hybridizing to target sequences (e.g., mRNA or cDNA sequence) of the above-disclosed genes under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip. Additionally probes for reference control/normalization genes are included.

Attached or immobilized as used herein to refer to a nucleic acid (e.g., a probe) and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The solid substrate can be a material that may be modified to contain discrete individual sites appropriate for the attachment or association of the probes and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate can be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The array/biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography. Detailed discussion of methods for linking nucleic acids to a support substrate can be found in, e.g., U.S. Pat. Nos. 5,837,832, 6,087,112, 5,215,882, 5,707,807, 5,807,522, 5,958,342, 5,994,076, 6,004,755, 6,048,695, 6,060,240, 6,090,556, and 6,040,138.

In some embodiments, an expressed transcript (e.g., a transcript of the AKAP4 gene) is represented in the nucleic acid arrays. In such embodiments, a set of binding sites can include probes with different nucleic acids that are complementary to different sequence segments of the expressed transcript. Examples of such nucleic acids can be of length of 15 to 200 bases, 20 to 100 bases, 25 to 50 bases, 40 to 60 bases. Each probe sequence can also include one or more linker sequences in addition to the sequence that is complementary to its target sequence. A linker sequence is a sequence between the sequence that is complementary to its target sequence and the surface of support. For example, the nucleic acid arrays of the invention can have one probe specific to each target microRNA gene. However, if desired, the nucleic acid arrays can contain at least 2, 5, 10, 100, 200, 300, 400, 500 or more probes specific to some expressed transcript.

In some embodiments, _AKAP4 RNAs or corresponding RT-PCR products can be pulled down using labelled probes that are complementary to AKAP4 nucleic acid sequences to identify AKAP4 target sequences. In general, the process for capture of a targeted nucleic acid is as follows: (1) nucleic acids are obtained from biological samples; (2) targeted nucleic acids are captured selectively by hybridizing the nucleic acids with complimentary DNA and/or RNA probes (i.e., baits); (3) nucleic acids not bound to the hybridization probes are washed away first, while targeted nucleic acids bound to the hybridization probes are eluted under appropriate conditions; and (4) the captured targeted nucleic acids are used for downstream applications. Such captured AKAP4 nucleic acid target sequences may be quantified using standard tools of molecular biology, such as for example PCR, Taqman assay, direct sequencing of RNA molecules, or RNA-seq (next generation sequencing). Exemplary procedures can be found in, e.g., the SureSelect Target Enrichment System™ marketed by Agilent Technologies, Inc. and US 20100029498, the contents of which are incorporated by reference in their entireties.

Kits

This invention further includes reagent kits and diagnostic systems containing reagents for performing the above-described methods, including methods for nucleic acid amplification, copying, primer extension, detection, identification, and/or quantification. To that end, one or more of the reaction components for the methods disclosed herein can be supplied in the form of a kit for use in the detection of a target nucleic acid. In such a kit, an appropriate amount of one or more reaction components is provided in one or more containers or held on a substrate (e.g., by electrostatic interactions or covalent bonding).

The kit described herein includes one or more of the primers described above. The kit can include one or more containers containing one or more primers of the invention. A kit can contain a single primer in a single container, multiple containers containing the same primer, a single container containing two or more different primers of the invention, or multiple containers containing different primers or containing mixtures of two or more primers. Any combination and permutation of primers and containers is encompassed by the kits of the invention.

The kit can also contain additional materials for practicing the above-described methods. In some embodiments, the kit contains some or all of the reagents, materials for performing a method according to the invention. The kit thus may comprise some or all of the reagents for performing a PCR reaction using the primer of the invention. Some or all of the components of the kits can be provided in containers separate from the container(s) containing the primer of the invention. Examples of additional components of the kits include, but are not limited to, one or more different polymerases, one or more primers that are specific for a control nucleic acid or for a target nucleic acid, one or more probes that are specific for a control nucleic acid or for a target nucleic acid, buffers for polymerization reactions (in 1× or concentrated forms), and one or more dyes or fluorescent molecules for detecting polymerization products. The kit may also include one or more of the following components: supports, terminating, modifying or digestion reagents, osmolytes, and an apparatus for detecting a detection probe.

The reaction components used in an amplification and/or detection process may be provided in a variety of forms. For example, the components (e.g., enzymes, nucleotide triphosphates, probes and/or primers) can be suspended in an aqueous solution or as a freeze-dried or lyophilized powder, pellet, or bead. In the latter case, the components, when reconstituted, form a complete mixture of components for use in an assay.

A kit or system may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target nucleic acid can be added to the individual tubes and amplification carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: reagents (including buffers) for isolating cells, reagent for lysis of cells, divalent cation chelating agents or other agents that inhibit unwanted nucleases, control DNA/RNA for use in ensuring that primers, the polymerase and other components of reactions are functioning properly, RNA isolation reagents (including buffers), amplification reaction reagents (including buffers), and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes for use in amplification or detection of target nucleic acids. In some embodiments, the kits can further include instructions to use the components in any of the methods described herein, e.g., a method using a crude matrix without nucleic acid extraction and/or purification.

The kits or system can also include packaging materials for holding the container or combination of containers. Typical packaging materials for such kits and systems include solid matrices (e.g., glass, plastic, paper, foil, microparticles and the like) that hold the reaction components or detection probes in any of a variety of configurations (e.g., in a vial, microtiter plate well, microarray, and the like).

A system, in addition to containing kit components, may further include instrumentation for conducting an assay, e.g. a luminometer for detecting a signal from a labeled probe and/or a magnetic device for separating nucleic acid hybridized to a capture probe.

Instructions, such as written directions or videotaped demonstrations detailing the use of the kits or system of the present invention, are optionally provided with the kit or systems. In a further aspect, the present invention provides for the use of any composition or kit herein, for the practice of any method or assay herein, and/or for the use of any apparatus or kit to practice any assay or method herein.

Optionally, the kits or systems of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

All of the above-described methods, reagents, and systems provide a variety of diagnostic tools which permit a blood-based, non-invasive assessment of disease status in a subject. Use of these methods, reagents, and systems in diagnostic tests, which may be coupled with other screening tests, such as a chest X-ray or CT scan, increase diagnostic accuracy and/or direct additional testing. In other aspects, the inventions described herein permit the prognosis of disease, monitoring response to specific therapies, and regular assessment of the risk of recurrence. The inventions described herein also permit the evaluation of changes in diagnostic signatures present in pre-surgery and post therapy samples and identifies a gene expression profile or signature that reflects tumor presence and may be used to assess the probability of recurrence. The results on pre- or post-surgery lung cancer identified in the examples below support a similar detectable effect of the tumor on gene expression in patient PBMCs A significant advantage of the methods of this invention over existing methods is that they are able to characterize the disease state from a minimally-invasive procedure, i.e., by taking a blood sample without isolating cancer cells. In contrast current practice for classification of cancer tumors from gene expression profiles depends on a tissue sample, usually a sample from a tumor. In the case of very small tumors, a biopsy is problematic and clearly if no tumor is known or visible, a sample from it is impossible. No purification or isolation of tumor is required, as is the case when tumor samples are analyzed. Blood samples have an additional advantage, which is that the material is easily prepared and stabilized for later analysis, which is important when messenger RNA is to be analyzed.

Additional Definitions

A "nucleic acid" refers to a DNA molecule (e.g., a cDNA or genomic DNA), an RNA molecule (e.g., an mRNA or cRNA), or a DNA or RNA analog. A DNA or RNA analog can be synthesized from nucleotide analogs. The nucleic acid molecule can be single-stranded or double-stranded, but preferably is double-stranded DNA.

As used herein, the term "target nucleic acid" or "target sequence" refers to a nucleic acid containing a target nucleic acid sequence. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid.

As used herein the term "amplification" and its variants includes any process for producing multiple copies or complements of at least some portion of a polynucleotide, said polynucleotide typically being referred to as a "template." The template polynucleotide can be single stranded or double stranded. A template may be a purified or isolated nucleic acid, or may be non-purified or non-isolated. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured.

In some embodiments, one round of amplification includes a given number of repetitions of a single cycle of amplification. For example, a round of amplification can include 5, 10, 15, 20, 25, 30, 35, 40, 50, or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis.

Amplification of this invention includes isothermal amplification. The term "isothermal" means conducting a reaction at substantially constant temperature, i.e., without varying the reaction temperature in which a nucleic acid polymerization reaction occurs. Isothermal temperatures for isothermal amplification reactions depend on the strand-displacing nucleic acid polymerase used in the reactions. Generally, the isothermal temperatures are below the melting temperature (Tm; the temperature at which half of the potentially double-stranded molecules in a mixture are in a single-stranded, denatured state) of the predominant reaction product, i.e., generally 90° C. or below, usually between about 20° C. and 75° C., and preferably between about 30° C. and 60° C., or more preferably at about 37° C.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotides (e.g., dNTP) capable of being incorporated into an extension product during amplification, i.e., DNA, RNA, or a derivative if DNA or RNA, which may include a label.

As used herein, the term "oligonucleotide" refers to a short polynucleotide, typically less than or equal to 300 nucleotides long (e.g., in the range of 5 and 150, preferably in the range of 10 to 100, more preferably in the range of 15 to 50 nucleotides in length). However, as used herein, the term is also intended to encompass longer or shorter polynucleotide chains. An "oligonucleotide" may hybridize to other polynucleotides, therefore serving as a probe for polynucleotide detection, or a primer for polynucleotide chain extension.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled with a label such as with biotin to which a streptavidin complex may later bind.

A "label" or "reporter molecule" is chemical or biochemical moiety useful for labeling a nucleic acid (including a single nucleotide), polynucleotide, oligonucleotide, or protein ligand, e.g., amino acid or antibody. Examples include fluorescent agents, chemiluminescent agents, chromogenic agents, quenching agents, radionucleotides, enzymes, substrates, cofactors, inhibitors, magnetic particles, and other moieties known in the art. Labels or reporter molecules are capable of generating a measurable signal and may be covalently or noncovalently joined to an oligonucleotide or nucleotide (e.g., a non-natural nucleotide) or ligand.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Hybridization" or "hybridize" or "anneal" refers to the ability of completely or partially complementary nucleic acid strands to come together under specified hybridization conditions (e.g., stringent hybridization conditions) in a parallel or preferably antiparallel orientation to form a stable double-stranded structure or region (sometimes called a "hybrid") in which the two constituent strands are joined by hydrogen bonds. Although hydrogen bonds typically form between adenine and thymine or uracil (A and T or U) or cytosine and guanine (C and G), other base pairs may form (e.g., Adams et al., The Biochemistry of the Nucleic Acids, 11th ed., 1992).

The term "stringent hybridization conditions" or "stringent conditions" means conditions in which a probe or oligomer hybridizes specifically to its intended target nucleic acid sequence and not to another sequence. Stringent conditions may vary depending well-known factors, e.g., GC content and sequence length, and may be predicted or determined empirically using standard methods well known to one of ordinary skill in molecular biology (e.g., Sambrook, J. et al., 1989, Molecular Cloning, A Laboratory Manual, 2nd ed., Ch. 11, pp. 11.47-11.57, (Cold Spring Harbor Laboratory Press, Cold Spring Harbor, N.Y.)).

"Stringent conditions" or 'high stringency conditions" typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (sodium chloride/sodium citrate, 0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 50% formamide at 55° C., followed by a high-stringency wash consisting of 0.1×SSC containing EDTA at 55° C.

"Moderately stringent conditions" may be identified conventionally and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like, by use of manufacturer's instructions (see, e.g., Illumina system instructions).

As used herein, the term "subject" refers to any organism having a genome, preferably, a living animal, e.g., a mammal, which has been the object of diagnosis, treatment, observation or experiment. Examples of a subject can be a human, a livestock animal (beef and dairy cattle, sheep, poultry, swine, etc.), or a companion animal (dogs, cats, horses, etc).

A "sample" as used herein means any biological fluid or tissue that contains the above-described low-density or mononuclear cells and/or cancer cells obtained from an organism (e.g., patient) or from components (e.g., blood) of an organism. The sample may be of any biological tissue, cell(s) or fluid. The sample may be a "clinical sample" which is a sample derived from a subject, such as a human patient or veterinary subject. The most suitable sample for use in this invention includes peripheral blood, more specifically low-density or mononuclear cells from peripheral blood. Other useful biological samples include, without limitation, whole blood, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a patient having cancer. Such samples may further be diluted with saline, buffer or a physiologically acceptable diluent. Alternatively, such samples are concentrated by conventional means. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, the term "cancer" refers to or describes the physiological condition in mammals that is typically characterized by unregulated cell growth. More specifically, as used herein, the term "cancer" means any lung cancer. In one embodiment, the lung cancer is NSCLC. In a more specific embodiment, the lung cancer is lung adenocarcinoma (AC or LAC). In another more specific embodiment, the lung cancer is lung squamous cell carcinoma (SCC or LSCC). In another embodiment, the lung cancer is a stage I or stage II NSCLC. In still another embodiment, the lung cancer is a mixture of early and late stages and types of NSCLC. The term "tumor," as used herein, refers to all neoplastic cell growth and proliferation, whether malignant or benign, and all pre-cancerous and cancerous cells and tissues.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. For example, "contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

As used herein the term "reference value" refers to a value that statistically correlates to a particular outcome when compared to an assay result. In preferred embodiments, the reference value is determined from statistical analysis of studies that compare RNA expression with known clinical outcomes. The reference value may be a threshold score value or a cutoff score value. Typically a reference value will be a threshold above (or below) which one outcome is more probable and below which an alternative outcome is more probable.

In one embodiment, a reference level may be one or more gene expression (e.g., in the form of mRNA) levels expressed as an average of the level of the expression from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, cell-containing samples are normalized by protein content or cell count. Nucleic acid samples may also be normalized relative to an internal control nucleic acid.

"Control" or "Control subject" as used herein refers to the source of the reference level (e.g., reference gene expression profiles) as well as the particular panel of control subjects identified in the examples below. For example, the control subject in one embodiment can be controls with lung cancer, such as a subject who is a current or former smoker with malignant disease, a subject with a solid lung tumor prior to surgery for removal of same; a subject with a solid lung tumor following surgical removal of said tumor; a subject with a solid lung tumor prior to therapy for same; and a subject with a solid lung tumor during or following therapy for same. In other embodiments, the controls for purposes of the compositions and methods described herein include any of the following classes of reference human subject with no lung cancer. Such non-healthy controls (NHC) include the classes of smoker with non-malignant disease, a former smoker with non-malignant disease (including patients with lung nodules), a non-smoker who has chronic obstructive pulmonary disease (COPD), and a former smoker with COPD. In still other embodiments, the control subject is a healthy non-smoker with no disease or a healthy smoker with no disease. In yet other embodiments, the control or reference is the same subject in which the genes or gene profile was assessed prior to surgery, or at another earlier time point to enable assessment of surgical or treatment efficacy or prognosis or progression of disease. Selection of the particular class of controls depends upon the use to which the diagnostic/monitoring methods and compositions are to be put by the physician.

In preferred embodiments, the selected control group, non-healthy controls, is specifically chosen to match as closely as possible the patients with malignant disease. The match includes both smoking status and smoking-related diseases such as COPD. All subjects of both classes can be either current or former smokers when they presented with symptoms of disease. The most informative genes disclosed herein can distinguish smokers with malignant disease from smokers with non-malignant disease.

The terms "determining," "measuring," "assessing," and "assaying" are used interchangeably and include both quantitative and qualitative measurement, and include determining if a characteristic, trait, or feature is present or not. Assessing may be relative or absolute. Assessing the presence of a target includes determining the amount of the target present, as well as determining whether it is present or absent.

As disclosed herein, the difference of the expression level of one or more genes is indicative of a disease or a stage thereof. The phrase "difference of the level" refers to differences in the quantity of a particular marker, such as a nucleic acid, in a sample as compared to a control or reference level. For example, the quantity of a particular biomarker (e.g., AKAP4) may be present at an elevated amount or at a decreased amount in samples of patients with a neoplastic disease compared to a reference level. In one embodiment, a "difference of a level" may be a difference between the quantity of a particular biomarker present in a sample as compared to a control (e.g., reference value) of at least about 1%, 2%, 3%, 5%, 10%, 15%, 20%, 25%, 30%, 35%, 40%, 50%, 60%, 75%, 80% 100%, 150%, 200%, or more. In one embodiment, a "difference of a level" may be a statistically significant difference between the quantities of a biomarker present in a sample as compared to a control. For example, a difference may be statistically significant if the measured level of the biomarker falls outside of about 1.0 standard deviation, about 1.5 standard deviations, about 2.0 standard deviations, or about 2.5 stand deviations of the mean of any control or reference group. With respect to mRNA measurement, the level may be measured from real-time PCR as the Ct value, which may be normalized to an ACt value as described in the Examples below.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

EXAMPLES

Example 1

In this example, materials and method for carrying out the assays in Examples 2 and 3 are described.

PBMC Collection

BD Vacutainer CPT tubes were used for PBMC fraction (PBMC and associated cells) collection in the manner described above according to manufacturer's instruction.

Total RNA Isolation

RNA was extracted from normal and lung cancer PBMC pellets using TRI Reagent (T9424 Sigma-Aldrich) according to the manufacturer instructions. Briefly, 1 ml of TRI Reagent was added to the pellet and incubated for 15 min at room temperature. 1 µl of linear acrylamide was added and incubated further for 5 min at room temperature. Then 100 µl of 1-bromo-3-chloropropane was added, vortexed for 30 seconds, incubated for 10 minutes at room temperature followed by centrifugation at 12000 g for 15 minutes at 4° C. The aqueous phase was collected and added 1 µl of RNasin (N2115 Promega), and 500 µl of isopropanol. After 10 minutes incubation at room temperature samples were centrifuged at 12000 g for 10 minutes at 4° C. The RNA pellet was washed twice with 1 ml of 75% ethanol. The pellet was air dried, and suspended in 50 µl of RNAse free water and stored at −80° C. RNA concentration and quality were assessed using the NanoDrop.

Reverse Transcription cDNA was synthesized from total RNA using the High Capacity cDNA Reverse Transcription Kit (Applied Biosystems, P/N 4374966) following the manufacturer's instructions. Briefly, 250 ng of total RNA was used as template in a total volume of 20 µl containing 2 µl 10×RT buffer, 0.8 µl 100 mM dNTP mix, 2 µl 10×RT Random Primers, 1 µl Multiscribe Reverse Transcriptase, and 1 µl RNase Inhibitor. The reactions were incubated at 25° C. for 10 minutes, 37° C. for 2 hours, and 85° C. for 5 min. The cDNA samples were stored at −20° C.

Quantitative Real Time PCR

The reference and genomic sequence for each gene included in the study was obtained from the UCSC Genome Bioinformatics website. RT-PCR primers were designed using Primer Express (Applied Biosystems). Gene specific primers were designed manually. Nested PCR was used to determine gene expression. PCR was used for the first round of amplification to selectively amplify the gene. PCR was carried out in 50 µl reaction containing 5 µl of cDNA, 10 µl 10× buffer, 1 µl 10 mM dNTP, 3 µl gene specific primer mix (20 µM), 5 units Taq Polymerase and amplified on a thermal cycler at 94° C. for 2 minutes followed by 40 cycles of 94° C. for 30 seconds, 60° C. for 1 min and 72° C. for 15 seconds, then 1 cycle of 72° C. for 10 min, ending at 4° C. The PCR primers for the 1$^{st}$ round amplification of AKAP4 are: 5' TCCTACATGATGGCGTACTCTG and 5' AAGTTGCCTTCTGAGCTGGAAC (SEQ ID NOs: 5 and 6, respectively). Real time PCR reactions were performed to detect the expression of gene in duplicate, in 25 µl reaction volume using 5 µl of 1$^{st}$ round PCR product, 12.5 µl SYBR Select Master Mix (Applied Biosystems), 0.25 µl primer mix (2 µM final) and 7.25 µl water. Ribosomal 5S gene is a housekeeping gene and was used for normalization. The real time PCR primers for AKAP4 are: 5' GGGTGTGTGCAAGGTAGATCTCT (SEQ ID NO: 7) and 5' CACATCGACAAAGCATATCACTTTC (SEQ ID NO: 8). The real time PCR primers for 5S are: 5' GCCATACCACCCTGAACG (SEQ ID NO: 9) and 5' AGCCTACAGCACCCGGTATT (SEQ ID NO: 10). As a negative control for contamination, wells without any template were also assayed. All reactions were carried out on the 7500 Fast Real Time PCR system (Applied Biosystem). The average of duplicate for each gene and sample was calculated using the ΔΔ threshold cycle (Ct) method and was normalized to the endogenous reference control gene 5S according to manufacturer's instructions.

Example 2

In this example, assays were conducted to identify and verify biomarkers for lung cancer diagnosis.

Briefly, cell populations containing PBMCs and associated cells were obtained in the manner described above from patients having NSCLC (late stage or early stage) and various control subjects. Then, assays were carried to out screen 120 genes that are expressed in the cell populations of lung cancer patients but not expressed or expressed at low levels in cell populations from normal smoking controls. It was found that the AKAP4 gene than can differentiate patients with lung cancer from healthy controls.

Then, quantitative RT-PCR was used to determine the AKAP4 gene expression in 264 NSCLC lung cancer patients and 135 age, gender and smoking history-matched healthy controls. To that end, the receiver operating characteristic (ROC) plot was used and the area under the receiver operating characteristic curve (AUC) and its 95% confidence interval were computed. It was known in that art that AUC can be interpreted as the probability that the result of a diagnostic test of a randomly selected abnormal subject will be greater than the result of the same diagnostic test from a randomly selected normal subject. The greater the AUC, the better the global performance of the diagnostic test.

It was found that the AUC of the ROC curve was 97.14% when all lung cancers are compared with healthy controls. Among these lung cancer cases, 133 were stage I NSCLC lung cancer. The results demonstrate that this AKAP4 biomarker in the cell population examined can differentiate lung cancer from smoking controls.

In addition, the AUC of the ROC curve is 97.9% when these stage I NSCLC are compared with healthy controls. Among the healthy controls, there are 24 patients with benign lung nodules which were confirmed by biopsy. The results demonstrate that AKAP4 can allow one to detect early stage NSCLC.

It was also found that the AUC of the ROC curve is 98.45% when all NSCLC lung cancers are compared with benign nodules. These results demonstrate that this biomarker can be used to distinguish lung cancer from benign nodules.

Additional assays were conducted to examine the tissue distribution for AKAP4 expression using RT-PCR described above. AKAP4 is expressed in lung cancer cell, such as by way of example A549, HCC827, H1975, H23 and H520, but not normal lung tissue. AKAP4 is expressed in normal adrenal gland and placenta. These results suggest that detection of AKAP4 from the NSCLC PBMC-containing cell fractions may come from circulating NSCLC cancer cells.

AKAP4 expressions in the whole blood cell samples from NSCLC patients and controls were also examined. It was found that there was no significant difference between NSCLC patients and controls when whole blood samples were used. See FIG. 1. These results indicate that whole blood samples do not allow one to use conventional detection method to detect AKAP4 expression to differentiate NSCLC from control presumably due to the extremely low relative numbers of circulating cancer cells in the whole blood which include abundant cell type as neutrophils not included in the PBMC fractions. That is, a very low number of lung cancer cells may circulate in the peripheral blood at very early stage. These cells were co-purified and enriched with PBMC and can be thus detected by examining AKAP4 expressions via the highly sensitive nested PCR.

Example 3

In this example, AKAP4 expressions in PBMC-containing cell fractions were monitored in longitudinal studies on four lung cancer patients at three different time points as shown in the table below to find out whether this circulating biomarker can be used to detect lung cancer recurrence.

|  | Time Point 1 | Time Point 3 | Time Point 3 |
| --- | --- | --- | --- |
| Patient #1 | pre-surgery | 6 months post-surgery | 12 months post-surgery |
| Patient #2 | pre-surgery | 9 months post-surgery | 24 months post-surgery |
| Patient #3 | pre-surgery | 9 months post-surgery | 36 months post-surgery |
| Patient #4 | 6 months post-surgery | 32 months post-surgery | 37 months post-surgery |

More specifically, in Patient #1, the AKAP4 expression was high before surgery and this patient was correctly classified as lung cancer based on AKAP4 expression. The AKAP4 expression dropped below the cut-off 6 months post-surgery, but then increased above the cut-off 12 months post-surgery. This bounce in AKAP4 expression suggested that this patient had recurrence of lung cancer at 12 months post-surgery. In fact, 4 month and 20 days later, it was found that this patient manifested clinical recurrence of lung cancer. These results indicated that AKAP4 expression in the PBMC-containing fraction samples can be used for early detection of recurrence and disease monitoring.

In Patient #2, it was found that the AKAP4 expression was also high before surgery and this patient was correctly classified as lung cancer based on AKAP4 expression. Like that in Patient #1, the AKAP4 expression in Patient #2 also dropped below the cut-off 9 months post-surgery. Yet, Patient #2's AKAP4 expression stayed below the cut-off at 24 months post-surgery. See FIG. 4. And, this patient did not have recurrence of lung cancer. These results indicated that AKAP4 expression in the PBMC fraction samples can be used for disease monitoring and prognosis.

A similar AKAP4 expression pattern and lung cancer outcome were found in Patient #3 too. The AKAP4 expression in PBMC-containing fraction of this patient was high before surgery and this patient was correctly classified as lung cancer based on AKAP4 expression. The AKAP4 expression dropped below the cut-off 9 months post-surgery and stayed below the cut-off 24 months post-surgery. Like Patient #2, Patient #3 also did not not have recurrence. These results again indicated that AKAP4 expression in the PBMC-containing fraction samples can be used for disease monitoring and prognosis.

PBMC-containing fraction samples were collected at 3 time points from lung cancer Patient #4 at 6 months post-surgery, 32 months post-surgery and 37 months post-surgery. The AKAP4 expression was found below the cut-off 6 months post-surgery. The AKAP4 expression then increased above the cut-off 32 months post-surgery, suggesting that this patient had lung cancer. Indeed, 2 month later, this patient manifested clinical recurrence of lung cancer. This patient then underwent radiotherapy and lung cancer nodule disappeared on CT scan after radiotherapy. The AKAP4 expression 3 months after radiotherapy dropped, but stayed above cut-off, suggesting radiotherapy was partially effective, but cancer remained after radiotherapy. In fact, this patient manifested metastatic lung cancer 10 months after radiotherapy. These results indicated that AKAP4 expression in the PBMC-containing fraction samples can be used for early detection of recurrence, disease monitoring, and prognosis.

Example 4

Cancer testis antigens ("CTA") genes were analyzed as blood based biomarkers for the detection of NSCLCs.

Figure 2A:
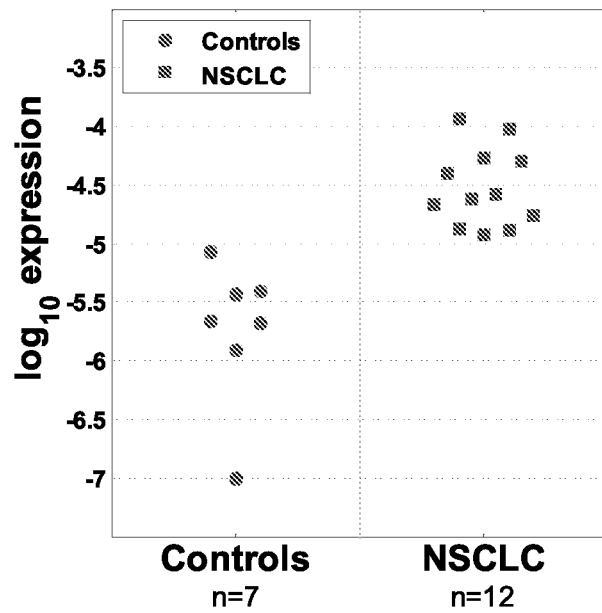
FIG. 2A illustrates that AKAP4 demonstrates perfect separation of samples from NSCLC and control groups based on its expression.
Figure 2B:
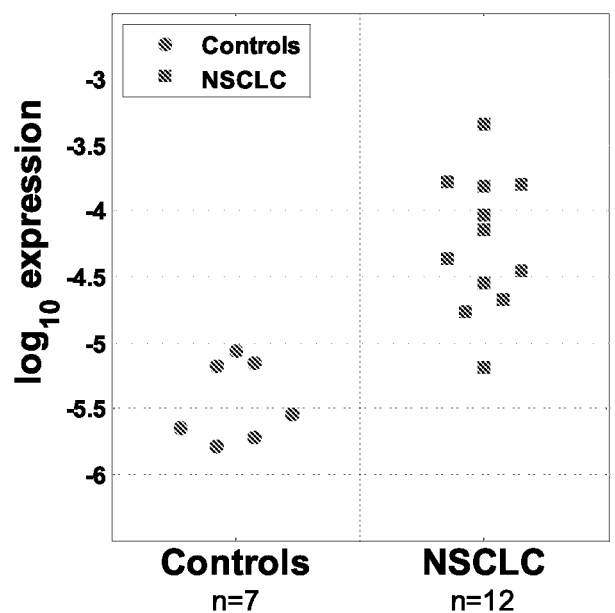
FIG. 2B illustrates that only 1 cancer sample was misclassified by expression of GAGE4

Unique PCR primers for 116 of the 130 CT genes on the X chromosome were designed (sequence similarities prevented the selection of specific primers for 14 CT-X genes) (Almeida L G, et al. *Nucleic Acids Res* 2009; 37(Database issue):D816-9). Nested PCR was applied as the detection method because it was likely mRNAs would be present at low levels in the PBMC fraction being tested. Tests were performed to determine whether any of the 116 CT-X genes were differentially expressed in PBMC derived RNA from a discovery set of 12 NSCLC lung cancer patients and 7 control patients with smoking related benign lung diseases including COPD and/or benign granulomatous inflammation. Four of the controls had histologically confirmed benign lung nodules. These highly characterized samples were a part of a previously described microarray study to develop blood based biomarkers for NSCLC (Showe M K, et al. *Cancer Res* 2009; 69(24):9202-10); Kossenkov A V, et al. *Clin Cancer Res* 2011; 17(18):5867-77). Based on results from the discovery set, two candidate CTX genes, AKAP4 and GAGE 4 that distinguished NSCLC from benign lung disease in this data set with the best accuracy were selected for further analysis on a larger independent sample set. Expression of AKAP4 perfectly separated cancer and control groups (FIG. 2A), while GAGE4 (FIG. 2B) misclassified only one NSCLC sample, among all 116 candidates tested. Thus, of the two biomarkers, AKAP4 was the most accurate and GAGE4 was later eliminated because of poor performance when applied to the larger data set.

Example 5

Figure 3A:
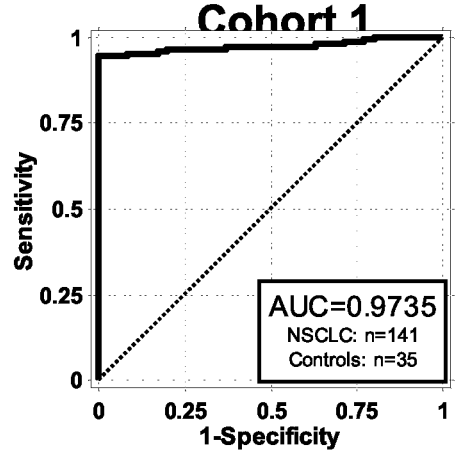
FIG. 3A illustrates the ROC curve of AKAP4 expression in the PBMC samples from 141 NSCLC patients and 35 patients with benign lung diseases.

In order to determine the potential utility of AKAP4 and GAGE4 as NSCLC biomarkers, an additional cohort of 141 NSCLC patients and 35 control patients with benign lung diseases which did not include any of the discovery set samples were analyzed. Twenty four of the 35 controls had lung nodules confirmed as benign by biopsy (Showe et al. 2009). Although the accuracy for both AKAP4 and GAGE4 were essentially identical on the small data set, the performance of AKAP4 expression on the larger data set was significantly higher than GAGE4 with an AUC for AKAP4 in this comparison of 0.9735 (FIG. 3A) and an AUC for GAGE4 of 0.7149. After testing and finding that combination of AKAP4 and GAGE4 expression did not improve overall prediction, and because of its low AUC in this larger sample set, GAGE4 were not included in the analysis going forward.

Figure 3B:
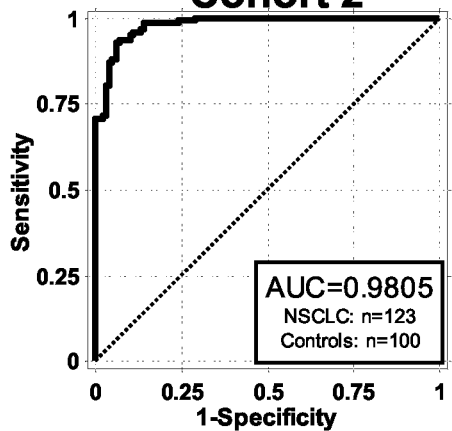
FIG. 3B illustrates that AKAP4 is validated as a circulating biomarker for NSCLC in the second independent patient cohort. ROC curve of AKAP4 expression in the PBMC samples from 123 NSCLC patients and 100 controls is shown.

AKAP4 expression was then assayed in a second independent cohort of patients. This data set included 123 NSCLC patients and 100 controls. The AUC of the ROC curve on the VII data set is 0.9805 (FIG. 3B).

Figure 3C:
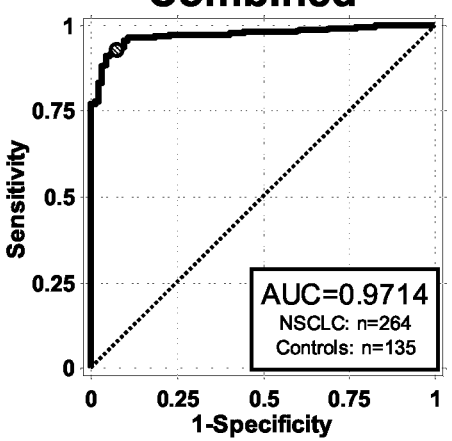
FIG. 3C illustrates that the ROC curve for the combined set of cohorts 1 and 2. The dot indicates the performance corresponding to selected optimal cutpoint.
Figure 3D:
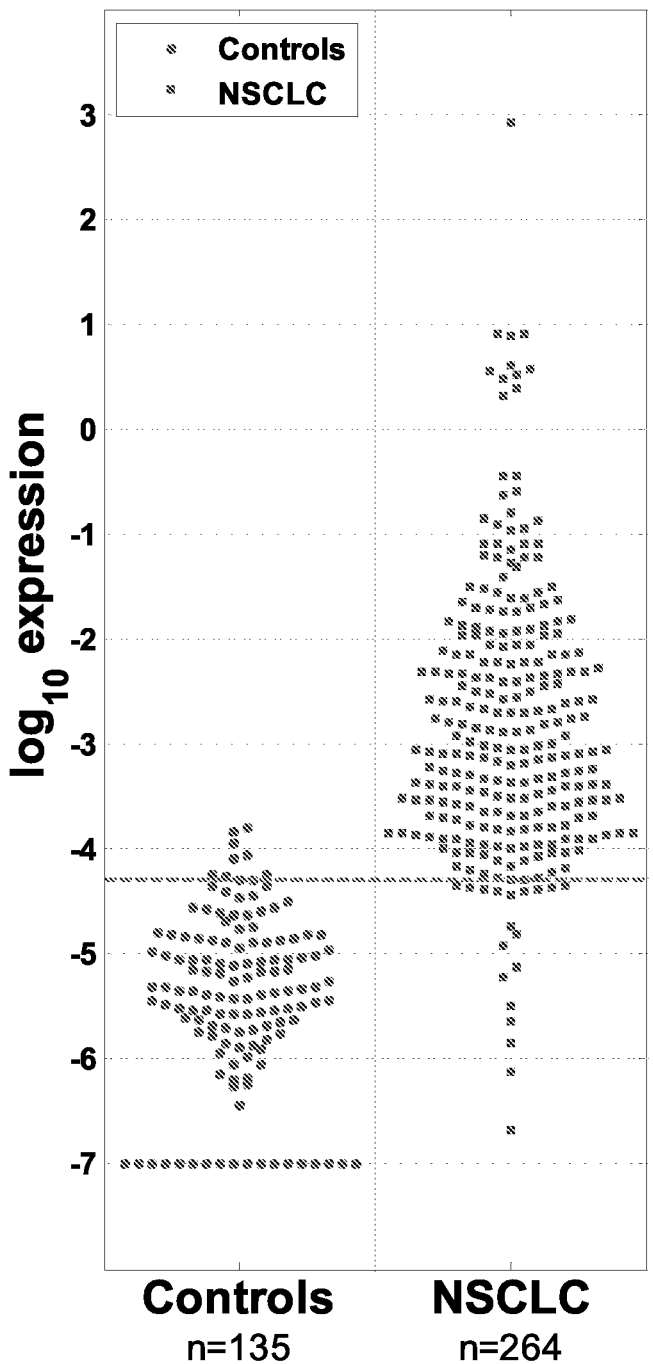
FIG. 3D illustrates the distribution of AKAP4 expression levels in NSCLC and controls. Green dotted line indicates cutpoint optimized for a balanced sensitivity (92.8%) and specificity (92.6%)

A combined data set that included the samples from both cohorts but not the discovery set was analyzed. The combined data included 264 NSCLC patients and 135 controls. Expression of AKAP4 as NSCLC classifier in the combined dataset the AUC of the ROC curve of 0.9714 (FIG. 3C) with the distribution of expression values between NSCLC and control groups shown in FIG. 3D were analyzed. The AKAP4 expression level of −4.3 showed the most balanced sensitivity/specificity values (92.8% and 92.6% respectively) for the total accuracy of 92.7%. Linear discriminant analysis with cross-validation that included in addition to AKAP4 expression, age, gender and smoking status as potential predictors did not show an improved AUC or accuracy. The final observed performances of AKAP4 expression for classifications are summarized in Table 1. In addition, cross-validation studies were performed in order to estimate variations of reported AUC and accuracy values (Table 2). Variation coefficient for the combined dataset was 0.10% for AUC and 0.16% for accuracy, indicating a very high result of confidence presented in the study.

TABLE 1

AKAP4 Expression In The Classification Of Different NSCLC And Controls Subsets

| Comparison | ROC AUC[95% CI] | Sens | Spec | Acc |
|---|---|---|---|---|
| Cohort 1<br>NSCLC n = 141<br>Controls n = 35 | 0.9735<br>[0.9516, 0.9953] | 90.8% | 100% | 92.6% |
| Cohort 2<br>NSCLC n= 123<br>Controls n = 100 | 0.9805<br>[0.9669, 0.9941] | 95.1% | 90.0% | 92.8% |
| Combined<br>NSCLC n = 264<br>Controls n = 135 | 0.9714<br>[0.9563, 0.9865] | 92.8% | 92.6% | 92.7% |
| Stage I VS<br>all Controls<br>Stage I n = 136<br>Controls n = 135 | 0.9795<br>[0.9650, 0.9939] | 93.4% | 92.6% | 93.0% |
| NSCLC vs<br>Nodules<br>NSCLC n = 264<br>Nodules n = 27 | 0.9825<br>[0.9691, 0.9958] | 92.8% | 100% | 93.5% |

Table 1 illustrates the performance of AKAP4 expression in the classification of different NSCLC and Controls subsets. For each classification the table lists observed AUC and 95% confidence interval (CI) and sensitivity (sens), specificity (spec) and overall accuracy (acc) for AKAP4 expression at a threshold of −4.3

Figure 4A:
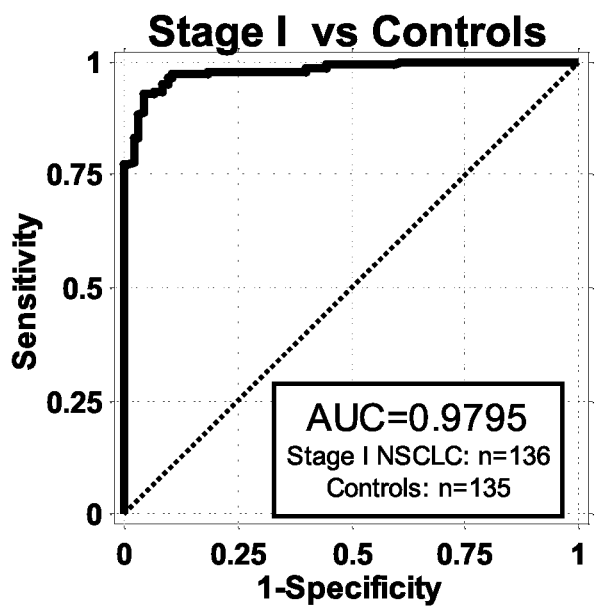
FIG. 4A illustrates the ROC curve of AKAP4 expression in the PBMC samples from 136 stage I NSCLC patients and 135 controls. AUC is 0.9795.
Figure 4B:
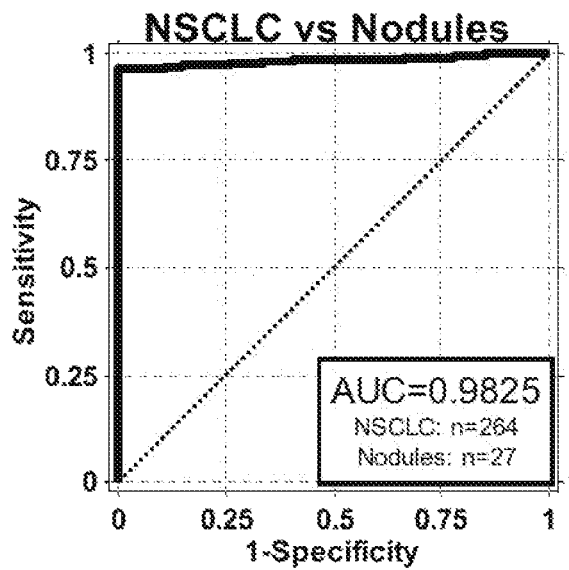
FIG. 4B illustrates the ROC curve of AKAP4 expression in the PBMC samples from 264 NSCLC patients and 27 patients with benign lung nodules. AUC is 0.9825.

There were two samples subgroups of special interest: Stage I NSCLC, a group that benefits most from early detection when lung resection is most favorable and high risk lung nodules which require surgical confirmation to determine the malignant/non-malignant status. Among the 264 NSCLC patients, 136 were diagnosed as stage I NSCLC. AKAP4 expression levels used as a classifier for just the stage I NSCLC and all controls demonstrated the AUC of the ROC curve of 0.9795 (FIG. 4A). Although the number of nodules included in this analysis is relatively small, the AUC of the ROC curve for classifying all 264 NSCLC vs 27 samples from patients with benign nodules gave a value of 0.9825 (FIG. 4B), the best performance of all tested classifications, indicating that AKAP4 expression associated with PBMC distinguishes benign from malignant lung nodules. AKAP4 provides a sensitive marker to track remission and act as an early marker of recurrence.

Example 6

Figure 5:
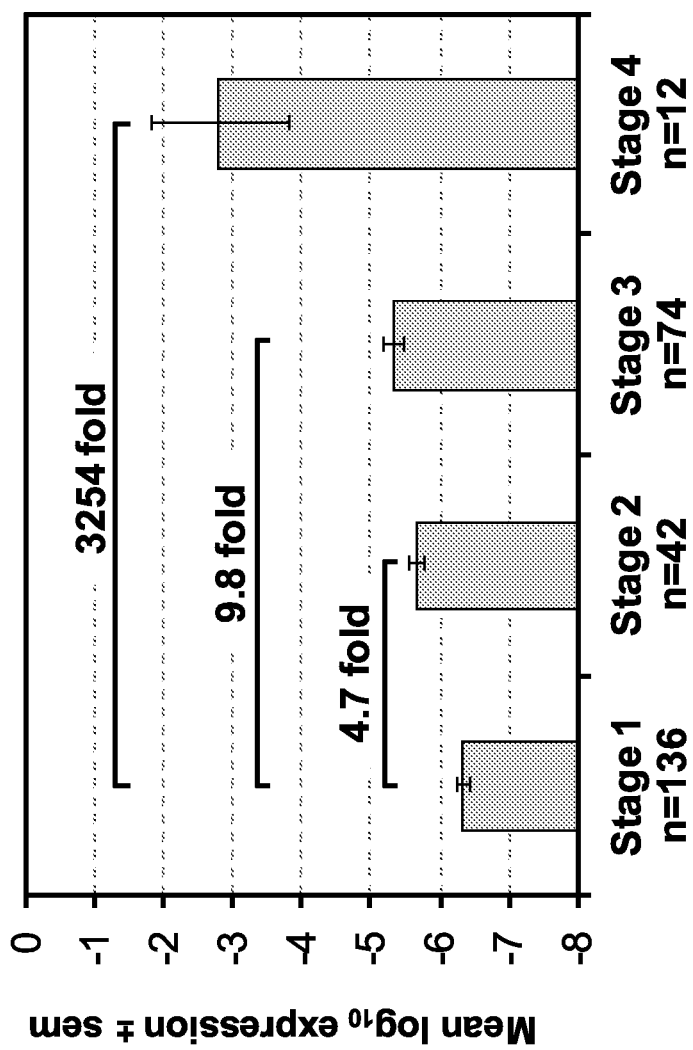
FIG. 5 illustrates that AKAP4 expression is associated with NSCLC stage. Average AKAP4 expression±standard error of mean is shown for each NSCLC Stage. Fold differences vs. Stage I are indicated.

Since in a previous PBMC gene expression study (Showe 2009 and Kossenkov 2011) it was determined that patients with lung squamous cell carcinomas (LSCC) were more accurately classified than those with lung adenocarcinomas (AC) and that classification accuracy also increased with advanced cancer stages, it was important to determine whether the strength of AKAP4 PCR signal also correlated with a variety of clinical parameters including cancer stage and subtype. Linear regression analysis of AKAP4 expression was performed using histology, stage, smoking history, gender and age as independent variables. The analysis identified that AKAP4 expression is significantly associated only with cancer stage (Table 2). FIG. 5 shows that magnitude of AKAP4 expression consistently increases through all 4 stages, with the stage II, III and IV levels of AKAP4 being respectively on average 4.7, 9.8 and >3000 times the expression level in stage I. The fact that AKAP4 expression did not associate significantly with tobacco use also demonstrates that the AKAP4 classification could be used successfully for higher risk current smokers as well as lower risk non-smokers with the same efficiency.

TABLE 2

| Variable | Significance (p < 0.05) | beta value | 95% CI |
| --- | --- | --- | --- |
| AC diagnosis | ns | −0.045 | [−0.581, 0.491] |
| LSCC diagnosis | ns | −0.01 | [−0.635, 0.614] |
| Stage | significant | 0.214 | [0.049, 0.379] |
| Never smokers | ns | −0.182 | [−0.822, 0.458] |
| Current smokers | ns | −0.008 | [−0.446, 0.431] |
| Years of smoking | ns | −0.009 | [−0.020, 0.001] |
| Packs per year | ns | −0.051 | [−0.284, 0.182] |
| Gender | ns | −0.028 | [−0.355, 0.298] |
| Age | ns | −0.012 | [−0.029, 0.005] |

Table 2 illustrates the results of linear regression analysis of AKAP4 expression and different clinical parameters. The results demonstrate that only tumor stage was significantly associated with AKAP4 expression.

That the origin of the AKAP4 signal detected is the lung cancer is further supported by the strong correlation of signal intensity to tumor stage as shown in FIG. 5. No other patient characteristic including age, gender, tobacco use or cancer subtype showed any significant correlation. The tumor derivation of this signal is further supported by data demonstrating that the AKAP4 presence in PBMC RNA is significantly reduced after successful lung resection and that expression increases once again with a lung tumor recurrence.

Figure 6:
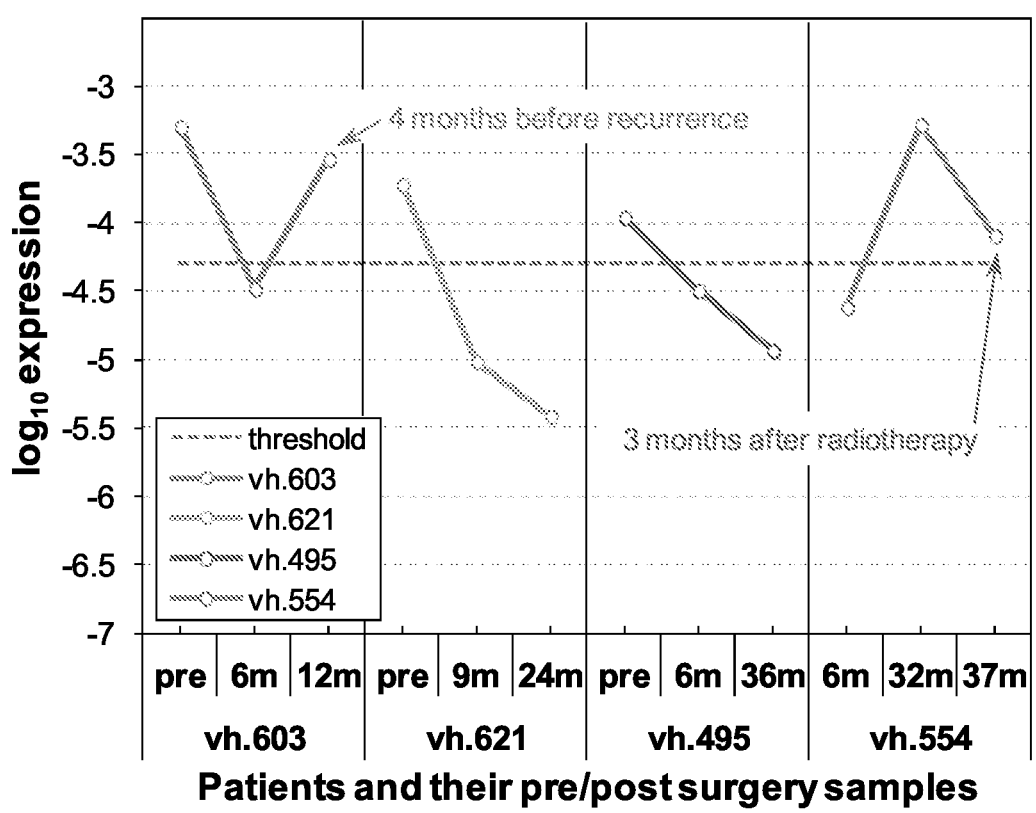
FIG. 6 illustrates that AKAP4 is a circulating biomarker for NSCLC disease monitoring and early detection of recurrence. (patient vh.603) AKAP4 expression is determined in PBMC samples from a NSCLC patient at three time points: pre-surgery; 6 months post-surgery; and 12 months post-surgery. The AKAP4 expression is high before surgery but drops below the cutpoint 6 months post-surgery, indicating the patient is in remission. AKAP4 expression increased above the cutpoint by 12 months post-surgery, indicating that this patient had lung cancer. Approximately 4 months after the positive AKAP4 result, a second lung cancer nodule was detected by CT scan. (patient vh.621) AKAP4 expression is determined in PBMC samples from a NSCLC patient at three time points: pre-surgery; 9 months post-surgery; and 24 months post-surgery. The AKAP4 expression is high prior to surgery. The AKAP4 expression dropped below the cutpoint at 9 months post-surgery and stayed below the cutpoint 24 months post-surgery. Follow-up CT scans have not detected any lung nodules. This patient is currently in remission. (patient vh.495) AKAP4 expression is determined in PBMC samples from a NSCLC patient at three time points: pre-surgery; 9 months post-surgery; and 36 months post-surgery. The AKAP4 expression is high prior to surgery. The AKAP4 expression dropped below cutpoint 9 months post-surgery and stayed below cutpoint 36 months post-surgery. Follow-up CT scans have not detected any lung nodules. This patient is currently assessed as being in remission. (patient vh.554) AKAP4 expression is determined in PBMC samples from a NSCLC patient at three time points: 6 months post-surgery; 32 months post-surgery; and 37 months post-surgery. The AKAP4 expression was below cutpoint 6 months post-surgery, suggesting this patient is in remission. The AKAP4 expression increased above cutpoint 32 months post-surgery indicating a recurrence. CT scan and subsequent biopsy confirmed recurrent NSCLC. The AKAP4 expression decreased 3 months after radiation therapy but stayed above cutpoint, suggesting a residual cancer presence remained. This patient was diagnosed with metastatic lung cancer 10 months after radiation therapy.

PBMC associated AKAP4 expression was analyzed after lung resection. Expression in samples from 4 NSCLC patients where follow up samples had been collected at several times after lung resection was analyzed. AKAP4 expression in pre-surgery samples were compared to expression at various times post-surgical resection. Four cases with somewhat different outcomes are shown in FIG. 6.

Case 1—Recurrence: Patient vh.603 is an 85 year-old female ex-smoker diagnosed as stage I NSCLC who underwent lung resection. CT scans were assessed in the follow-ups and PBMC samples were collected at 3 time points from this patient: pre-surgery, 6 months post-surgery, and 12 months post-surgery. Approximately 16 months after surgery, a lung nodule was found by CT scan and subsequently confirmed as NSCLC. Nested PCR was carried out on all available samples and the cutpoint was used on the large dataset to assess AKAP4 expression. The AKAP4 expression in the pre-surgery sample was above the cutpoint, confirming the presence of NSCLC, which was in agreement with the clinical diagnosis (FIG. 6). The AKAP4 expression dropped to below the cutpoint in the 6 months post-surgery sample, indicating that the patient was in remission at 6 months (FIG. 6) based on our case control study. Expression subsequently increased to above cutpoint in the 12 months post-surgery sample, suggesting the cancer had recurred (FIG. 6) although no evidence of recurrence was detected by CT scan at this time. Approximately 4 months later (16 months post-surgery), a lung nodule was detected by CT scan and subsequently confirmed as NSCLC.

Case 2—Remission: Patient vh.621 is an 85 year-old female ex-smoker, diagnosed with Stage I NSCLC. The patient's tumor was removed by surgery and the patient was diagnosed as in remission. PBMC samples were collected at 3 time points: pre-surgery, 9 months post-surgery, and 24 months post-surgery. AKAP4 expression in the pre-surgery sample was above the cutpoint, consistent with the presence of a NSCLC (FIG. 6). The AKAP4 expression dropped below the cutpoint at 9 months post-surgery and remained below the cutpoint 24 months post-surgery (FIG. 5). By clinical assessment this patient was in remission.

Case 3—Remission: Patient vh.495 is a 67 year-old female ex-smoker also diagnosed as stage I NSCLC. PBMC were collected at 3 time points from this patient: pre-surgery, 9 months post-surgery, and 36 months post-surgery. The AKAP4 expression dropped from above the cutpoint before surgery to below the cutpoint 9 months after surgery and remained below the cutpoint at 36 months post-surgery (FIG. 6). Repetitive CT scans confirm that this patient was in remission.

Case 4—Recurrence+treatment: AKAP4 expression in PBMC samples from a patient who relapsed and subsequently underwent additional treatment was determined. Patient vh.554 is a 79 year-old female current smoker diagnosed as stage I NSCLC. Surgery was performed to remove her tumor and 32 months later, a lung nodule was detected by CT scans during follow-up. The nodule was confirmed as NSCLC by biopsy. This patient underwent stereotactic body radiation therapy. CT scans after radiation therapy did not detect the presence of any lung nodule. However, metastatic disease was detected 12 months after the finding of the second tumor. AKAP4 expression in this patient's blood was analyzed at 3 time points from this patient: 6 month post-surgery, 32 months post-surgery, which was at the time of recurrence detection but pre-radiation therapy, and 37 months post-surgery (3 months post-radiation). A pre-surgery blood sample was not available. While the AKAP4 expression was below the cutpoint 6 months post-surgery (FIG. 6), expression was increased significantly above the cutpoint 32 months post-surgery supporting the CT and biopsy diagnosis of a NSCLC recurrence. At 37 months post-surgery (3 months post-radiation therapy) AKAP4 levels decreased from pre-radiation therapy values but remained above the cutpoint, indicating the presence of residual cancer, even though the CT scan did not detect any lung nodule at that time and no clinical indication of residual disease. This patient was clinically diagnosed as metastatic NSCLC 10 months post-radiotherapy. These clinical studies support the utility of monitoring AKAP4 expression as a marker of remission/recurrence even in the absence of a positive CT scan.

Patients vh.603, vh.621 and vh.495 show a significant drop in AKAP4 expression between the pre and post-surgery samples. AKAP4 expression for patients vh.623 and vh.495, who remained in remission 24 and 36 months post-surgery respectively remain below the cut-off value. Patient vh.603 had a sharp rise in AKAP4 expression 12 months post-surgery and 4 months prior to being diagnosed with a recurrence. The pre-surgery sample for patient vh.554 was not available but the 6 month post-surgery sample is in the non-cancer range. Patient vh.554 showed a sharp increase in AKAP4 at 32 months post-surgery associated with a diagnosed recurrence and underwent radiotherapy. The AKAP4 signal at the $3^{rd}$ time point, 3 months after radiotherapy has greatly decreased but remains in the cancer range. It was unexpectedly determined that there was a strong correlation between the presence of a tumor in the lung and the detection of AKAP4 message in the peripheral blood samples.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method comprising:
   providing a population of low-density cells from blood of a human test subject;
   obtaining a first expression level of RNA transcribed from the AKAP4 gene of the population of low-density cells;
   comparing the first expression level with a first predetermined reference value; and
   administering to the human test subject an agent to treat non-small cell lung cancer (NSCLC) when the first expression level is above the first predetermined reference value.

2. The method of claim 1, wherein the first predetermined reference value is obtained from a control subject selected from the group consisting of the followings:
   (a) a smoker with malignant disease,
   (b) a smoker with non-malignant disease,
   (c) a former smoker with non-malignant disease,
   (d) a healthy non-smoker with no disease,
   (e) a non-smoker who has chronic obstructive pulmonary disease (COPD),
   (f) a former smoker with COPD,
   (g) a subject with a solid lung tumor prior to surgery for removal of same;
   (h) a subject with a solid lung tumor following surgical removal of said tumor,
   (i) a subject with a solid lung tumor prior to therapy for same, and
   (j) a subject with a solid lung tumor during or following therapy for same,
   wherein said control subject (a)-(j) is the same test subject at a temporally earlier time point.

3. The method of claim 1, further comprising determining that the human test subject has or is at risk of having NSCLC when the first expression level is above the first predetermined reference value obtained from a control subject that does not have lung cancer.

4. The method of claim 1, further comprising extracting total RNA from the population of low-density cells prior to the step of obtaining.

5. The method of claim 4, wherein the obtaining step is conducted by a process comprising Quantitative-Real Time-Polymerase Chain Reaction (qRT-PCR).

6. The method of claim 5, wherein the process further comprises nested qRT-PCR.

7. The method of claim 6, wherein the nested qRT-PCR is conducted with a first pair of primers and a second pair of primers that produce a first amplicon and a second amplicon, respectively.

8. The method of claim 7, wherein the first pair of primers comprises the sequences of SEQ ID NOs: 5 and 6.

9. The method of claim 7, wherein the second pair of primers comprises the sequences of SEQ ID NOs: 7 and 8.

10. The method of claim 1, wherein the obtaining step comprises contacting the cells, RNAs thereof, or cDNAs produced therefrom with a probe that hybridizes to an RNA or cDNA of the AKAP4 gene or the complement thereof under a stringent condition.

11. The method of claim 10, wherein the probe is deposited onto a solid support.

12. The method of claim 1, wherein the method further comprises obtaining a second expression level of a second gene selected from the group consisting of
   (a) an expression level of hepatitis B virus x associated protein (HBXAP or RSF1),
   (b) an expression level of dual-specificity tyrosine-(Y)-phosphorylation regulated kinase 2 (DYRK2),
   (c) an expression level of YY1 transcription factor (YY1),
   (d) an expression level of chromosome 19 open reading frame 12, transcript variant 1 (C19orfl2),
   (e) an expression level of thioesterase superfamily member 2 (THEM2),
   (f) an expression level of triple functional domain (PT-PRF interacting) (TRIO),
   (g) an expression level of myeloid-associated differentiation marker, transcript variant 4 (MYADM),
   (h) an expression level of BA11-associated protein 2 (BAIAP2),
   (i) an expression level of leucine zipper domain protein (FLJ22386 or ROGDI),
   (j) an expression level of DnaJ (Hsp40) homo log, subfamily B, member 14 (DNAJB14),
   (k) an expression level of brain and reproductive organ-expressed TNFRSF1A modulator (BRE),
   (l) an expression level of transmembrane protein 41A (TMEM41A),
   (m) an expression level of chromosome 9 open reading frame 64 (C9orf64),
   (n) an expression level of chromosome 20 open reading frame 55, transcript variant 1 (C20orf55 or FAM110A),
   (o) an expression level of pecanex-like 2 PCNXL2,
   (p) an expression level of RE1-silencing transcription factor (REST),
   (q) an expression level of HSPC142 protein (HSPC142 or C19orf62),
   (r) an expression level of hypothetical protein BC015148 (LOC93081 or C13orf27),
   (s) an expression level of activating signal cointegrator 1 complex subunit 3 (ASCC3),
   (t) an expression level of solute carrier family 1, member 5 (SLC1A5),
   (u) an expression level of protein tyrosine phosphatase-like A domain containing 1 (PTPLAD1),
   (v) an expression level of MRE1 lmeiotic recombination 11 homolog A (MRE11A),
   (w) an expression level of hypothetical protein or GTP-binding protein 10 (DKFZP686A10121 or GTPBP10),
   (y) an expression level of Soares fetal liver spleen 1NFLS cDNA clone IMAGp998K18127,
   (z) an expression level of serpin peptidase inhibitor, clade I (pancpin), member 2 (SERPINI2),
   (aa) an expression level of cDNA FLJ44370 fis, clone TRACH3008902 or CAMP responsive element binding protein 1 (CREB1),
   (bb) an expression level of coiled-coil domain containing 53 (CCDC53),
   (cc) an expression level of ubiquitin specific peptidase 48 (USP48), and
   (dd) an expression level of zinc finger and SCAN domain containing 2, transcript variant 3 (ZSCAN2),
   comparing the second expression level of the second gene with a second predetermined reference value; and
   determining that the human test subject has or is at risk of having NSCLC when (i) the first expression level is above the first predetermined reference value obtained from a control subject that does not have lung cancer and (ii) the second expression level is above the second predetermined reference value obtained from a control subject that does not have lung cancer.

13. The method of claim 1, further comprising additional evaluation of the human test subject, wherein said additional evaluation comprises one or more of a diagnosis of a lung cancer, a diagnosis of a stage of lung cancer, a diagnosis of a type or classification of a lung cancer, a diagnosis or detection of a recurrence of a lung cancer, a diagnosis or detection of a regression of a lung cancer, a prognosis of a lung cancer, or an evaluation of the response of a lung cancer to a surgical or non-surgical therapy.

14. The method of claim 1, wherein said human test subject has undergone surgery for solid tumor resection or chemotherapy.

* * * * *

```
                              SEQUENCE LISTING

<160> NUMBER OF SEQ ID NOS: 10

<210> SEQ ID NO 1
<211> LENGTH: 2881
<212> TYPE: DNA
<213> ORGANISM: Homo sapiens

<400> SEQUENCE: 1
ccagctggca gtcaaggctg taggagggca tggagagttg aagaaaaaag cagtatcttg      60
aggcagactg gaagagtcat cacagcatcc aaatcaacaa gaaaacatca ttccagggtc     120
ctacatgatg gcgtactctg atactacaat gatgtctgat gatattgact ggttacgcag     180 ccacagggt gtgtgcaagg tagatctcta caacccagaa ggacagcaag atcaggaccg      240
gaaagtgata tgctttgtcg atgtgtccac cctgaatgta aagataaag attacaagga     300 tgctgctagt tccagctcag aaggcaactt aaacctggga agtctggaag aaaaagagat     360
tatcgtgatc aaggacactg agaagaaaga ccagtctaag acagagggat ctgtatgcct     420
tttcaaacaa gctccctctg atcctgtaag tgtcctcaac tggcttctca gtgatctcca     480
gaagtatgcc ttgggtttcc aacatgcact gagcccctca acctctacct gtaaacataa     540
agtaggagac acagagggcg aatatcacag agcatcctct gagaactgct acagtgtcta     600
tgccgatcaa gtgaacatag attatttgat gaacagacct caaaacctac gtctagaaat     660
gacagcagct aaaaacacca acaataatca aagtccttca gctcctccag ccaaacctcc     720
tagcactcag agagcagtca tttcccctga tggagaatgt tctatagatg accttttcctt    780 ctacgtcaac cgactatctt ctctggtaat ccagatggcc cataaggaaa tcaaggagaa     840
gttggaaggt aaaagcaaat gccttcatca ttcaatctgt ccatcccctg gaacaaaga      900 gagaatcagt ccccgaactc ctgcgagcaa gattgcttct gaaatggcct atgaagctgt     960
ggaactgaca gctgcagaaa tgcgtggcac tggagaggag tccagggaag gtggccagaa    1020
aagctttcta tatagcgaat tatccaacaa gagcaaaagt ggagacaaac agatgtccca    1080
gagagagagc aaagaatttg cagattccat cagcaagggg ctcatggttt atgcaaatca    1140
ggtggcatct gacatgatgg tctctctcat gaagaccttg aaagtgcaca gctctgggaa    1200
gccaattcca gcatctgtgg tcctgaagag ggtgttgcta aggcacacca aggagattgt    1260
gtccgatttg attgattctt gcatgaagaa cctgcataat attactgggg tcctgatgac    1320
tgactcagac tttgtctcag ctgtcaagag aaatctgttc aaccagtgga acaaaatgc     1380 tacagacatc atggaggcca tgctgaagcg cttggtcagt gcccttatag gtgaggagaa    1440
ggagactaag tctcagagtc tgtcatatgc atctttaaaa gctgggtccc atgatcccaa    1500
atgcaggaat cagagtcttg aattctccac catgaaagct gaaatgaaag agagggacaa    1560
aggcaaaatg aaatcagacc catgcaagtc actgactagt gctgagaaag tcggtgaaca    1620
cattctcaaa gagggcctaa ccatctggaa ccaaaagcaa ggaaactcat gcaaggtggc    1680
taccaaagca tgcagcaata aagatgagaa aggagaaag atcaatgctt ccacagattc     1740 actgccaag gacctgattg tctctgccct taagctgatc cagtaccatc tgacccagca     1800
gactaagggc aaagatacat gtgaagaaga ctgtcctggt tccaccatgg gctatatggc    1860
tcagagtact caatatgaaa agtgtggagg tggccaaagt gccaaagcac tttcagtgaa    1920
```

```
acaactagaa tctcacagag cccctggacc atccacctgt caaaaggaga accaacacct    1980
ggactcccag aaaatggata tgtcaaacat cgttctaatg ctgattcaga aactgcttaa    2040
tgagaacccc ttcaaatgtg aggatccatg cgaaggtgag aacaagtgtt ctgagcccag    2100
ggcaagcaaa gcagcttcca tgtccaacag atctgacaaa gcggaagaac aatgccagga    2160
gcatcaagaa cttgactgta ccagtgggat gaagcaagcg aacgggcaat ttatagataa    2220
actagtagaa tctgtgatga agctctgcct tatcatggct aagtatagca acgatggggc    2280
agcccttgct gagttggaag aacaagcagc ctcggcaaat aagcccaatt tcaggggcac    2340
cagatgcatt cacagtggtg caatgccaca gaactatcaa gactctcttg gacatgaagt    2400
aattgtcaat aatcagtgct ctacaaatag cttgcagaag cagctccagg ctgtcctgca    2460
gtggattgca gcctcccagt ttaacgtgcc catgctctac ttcatgggag ataaggatgg    2520
acaactggaa aagcttcctc aggtttcagc taaagcagca gagaagggt acagtgtagg    2580 aggtcttctt caagaggtca tgaagtttgc caaggaacgg caaccagatg aagctgtggg    2640
aaaggtggcc aggaaacagt tgctggactg gctgctcgct aacctgtgag ctgatccttg    2700
actcctcttc atcttagccc ccctagcagc attccatccc agccagagca ccccaccat    2760 caggccagtc aactgcacaa tacacaactg tatttcccaa tacacttgag cagttgcctg    2820
tgaatgtaag aggtgtcaac aaactgggaa ataaaataaa aaaaaataat aataaatgtg    2880
t                                                                    2881

<210> SEQ ID NO 2
<211> LENGTH: 854
<212> TYPE: PRT
<213> ORGANISM: Homo sapiens

<400> SEQUENCE: 2

Met Met Ala Tyr Ser Asp Thr Thr Met Met Ser Asp Asp Ile Asp Trp
1               5                   10                  15

Leu Arg Ser His Arg Gly Val Cys Lys Val Asp Leu Tyr Asn Pro Glu
            20                  25                  30

Gly Gln Gln Asp Gln Asp Arg Lys Val Ile Cys Phe Val Asp Val Ser
        35                  40                  45

Thr Leu Asn Val Glu Asp Lys Asp Tyr Lys Asp Ala Ala Ser Ser Ser
    50                  55                  60

Ser Glu Gly Asn Leu Asn Leu Gly Ser Leu Glu Glu Lys Glu Ile Ile
65                  70                  75                  80

Val Ile Lys Asp Thr Glu Lys Lys Asp Gln Ser Lys Thr Glu Gly Ser
                85                  90                  95

Val Cys Leu Phe Lys Gln Ala Pro Ser Asp Pro Val Ser Val Leu Asn
            100                 105                 110

Trp Leu Leu Ser Asp Leu Gln Lys Tyr Ala Leu Gly Phe Gln His Ala
        115                 120                 125

Leu Ser Pro Ser Thr Ser Thr Cys Lys His Lys Val Gly Asp Thr Glu
    130                 135                 140

Gly Glu Tyr His Arg Ala Ser Ser Glu Asn Cys Tyr Ser Val Tyr Ala
145                 150                 155                 160

Asp Gln Val Asn Ile Asp Tyr Leu Met Asn Arg Pro Gln Asn Leu Arg
                165                 170                 175

Leu Glu Met Thr Ala Ala Lys Asn Thr Asn Asn Gln Ser Pro Ser
            180                 185                 190
```

-continued

```
Ala Pro Pro Ala Lys Pro Pro Ser Thr Gln Arg Ala Val Ile Ser Pro
            195                 200                 205

Asp Gly Glu Cys Ser Ile Asp Asp Leu Ser Phe Tyr Val Asn Arg Leu
210                 215                 220

Ser Ser Leu Val Ile Gln Met Ala His Lys Glu Ile Lys Glu Lys Leu
225                 230                 235                 240

Glu Gly Lys Ser Lys Cys Leu His His Ser Ile Cys Pro Ser Pro Gly
                245                 250                 255

Asn Lys Glu Arg Ile Ser Pro Arg Thr Pro Ala Ser Lys Ile Ala Ser
            260                 265                 270

Glu Met Ala Tyr Glu Ala Val Glu Leu Thr Ala Ala Glu Met Arg Gly
        275                 280                 285

Thr Gly Glu Glu Ser Arg Glu Gly Gln Lys Ser Phe Leu Tyr Ser
    290                 295                 300

Glu Leu Ser Asn Lys Ser Lys Ser Gly Asp Lys Gln Met Ser Gln Arg
305                 310                 315                 320

Glu Ser Lys Glu Phe Ala Asp Ser Ile Ser Lys Gly Leu Met Val Tyr
                325                 330                 335

Ala Asn Gln Val Ala Ser Asp Met Met Val Ser Leu Met Lys Thr Leu
            340                 345                 350

Lys Val His Ser Ser Gly Lys Pro Ile Pro Ala Ser Val Val Leu Lys
        355                 360                 365

Arg Val Leu Leu Arg His Thr Lys Glu Ile Val Ser Asp Leu Ile Asp
    370                 375                 380

Ser Cys Met Lys Asn Leu His Asn Ile Thr Gly Val Leu Met Thr Asp
385                 390                 395                 400

Ser Asp Phe Val Ser Ala Val Lys Arg Asn Leu Phe Asn Gln Trp Lys
                405                 410                 415

Gln Asn Ala Thr Asp Ile Met Glu Ala Met Leu Lys Arg Leu Val Ser
            420                 425                 430

Ala Leu Ile Gly Glu Lys Glu Thr Lys Ser Gln Ser Leu Ser Tyr
        435                 440                 445

Ala Ser Leu Lys Ala Gly Ser His Asp Pro Lys Cys Arg Asn Gln Ser
450                 455                 460

Leu Glu Phe Ser Thr Met Lys Ala Glu Met Lys Glu Arg Asp Lys Gly
465                 470                 475                 480

Lys Met Lys Ser Asp Pro Cys Lys Ser Leu Thr Ser Ala Glu Lys Val
                485                 490                 495

Gly Glu His Ile Leu Lys Glu Gly Leu Thr Ile Trp Asn Gln Lys Gln
            500                 505                 510

Gly Asn Ser Cys Lys Val Ala Thr Lys Ala Cys Ser Asn Lys Asp Glu
        515                 520                 525

Lys Gly Glu Lys Ile Asn Ala Ser Thr Asp Ser Leu Ala Lys Asp Leu
    530                 535                 540

Ile Val Ser Ala Leu Lys Leu Ile Gln Tyr His Leu Thr Gln Gln Thr
545                 550                 555                 560

Lys Gly Lys Asp Thr Cys Glu Glu Asp Cys Pro Gly Ser Thr Met Gly
                565                 570                 575

Tyr Met Ala Gln Ser Thr Gln Tyr Glu Lys Cys Gly Gly Gln Ser
            580                 585                 590

Ala Lys Ala Leu Ser Val Lys Gln Leu Glu Ser His Arg Ala Pro Gly
        595                 600                 605

Pro Ser Thr Cys Gln Lys Glu Asn Gln His Leu Asp Ser Gln Lys Met
```

Asp Met Ser Asn Ile Val Leu Met Leu Ile Gln Lys Leu Leu Asn Glu
625                 630                 635                 640

Asn Pro Phe Lys Cys Glu Asp Pro Cys Glu Gly Asn Lys Cys Ser
            645                 650                 655

Glu Pro Arg Ala Ser Lys Ala Ala Ser Met Ser Asn Arg Ser Asp Lys
            660                 665                 670

Ala Glu Glu Gln Cys Gln Glu His Gln Glu Leu Asp Cys Thr Ser Gly
            675                 680                 685

Met Lys Gln Ala Asn Gly Gln Phe Ile Asp Lys Leu Val Glu Ser Val
690                 695                 700

Met Lys Leu Cys Leu Ile Met Ala Lys Tyr Ser Asn Asp Gly Ala Ala
705                 710                 715                 720

Leu Ala Glu Leu Glu Glu Gln Ala Ala Ser Ala Asn Lys Pro Asn Phe
            725                 730                 735

Arg Gly Thr Arg Cys Ile His Ser Gly Ala Met Pro Gln Asn Tyr Gln
            740                 745                 750

Asp Ser Leu Gly His Glu Val Ile Val Asn Asn Gln Cys Ser Thr Asn
            755                 760                 765

Ser Leu Gln Lys Gln Leu Gln Ala Val Leu Gln Trp Ile Ala Ala Ser
770                 775                 780

Gln Phe Asn Val Pro Met Leu Tyr Phe Met Gly Asp Lys Asp Gly Gln
785                 790                 795                 800

Leu Glu Lys Leu Pro Gln Val Ser Ala Lys Ala Ala Glu Lys Gly Tyr
            805                 810                 815

Ser Val Gly Gly Leu Leu Gln Glu Val Met Lys Phe Ala Lys Glu Arg
            820                 825                 830

Gln Pro Asp Glu Ala Val Gly Lys Val Ala Arg Lys Gln Leu Leu Asp
            835                 840                 845

Trp Leu Leu Ala Asn Leu
    850

<210> SEQ ID NO 3
<211> LENGTH: 2867
<212> TYPE: DNA
<213> ORGANISM: Homo sapiens

<400> SEQUENCE: 3
caggggtggc agccaactgc aggtgcccaa gaacttggca cttctcagtt ccatctaaag      60
gggcacatct cccttctggg tgtcacgttt tcagccaaac atctaaaaga acttcatcat     120
caagatgtct gatgatattg actggttacg cagccacagg ggtgtgtgca aggtagatct     180
ctacaaccca gaaggacagc aagatcagga ccggaaagtg atatgctttg tcgatgtgtc     240
cacccctgaat gtagaagata aagattacaa ggatgctgct agttccagct cagaaggcaa     300
cttaaacctg ggaagtctgg aagaaaaaga gattatcgtg atcaaggaca ctgagaagaa     360
agaccagtct aagacagagg gatctgtatg ccttttcaaa caagctccct ctgatcctgt     420
aagtgtcctc aactggcttc tcagtgatct ccagaagtat gccttgggtt ccaacatgc     480
actgagcccc tcaacctcta cctgtaaaca taaagtagga gacacagagg gcgaatatca     540
cagagcatcc tctgagaact gctacagtgt ctatgccgat caagtgaaca tagattattt     600
gatgaacaga cctcaaaacc tacgtctaga aatgacagca gctaaaaaca ccaacaataa     660
tcaaagtcct tcagctcctc cagccaaacc tcctagcact cagagagcag tcatttcccc     720

| | | |
|---|---|---|
| tgatggagaa tgttctatag atgacctttc cttctacgtc aaccgactat cttctctggt | 780 | |
| aatccagatg gcccataagg aaatcaagga gaagttggaa ggtaaaagca aatgccttca | 840 | |
| tcattcaatc tgtccatccc ctgggaacaa agagagaatc agtccccgaa ctcctgcgag | 900 | |
| caagattgct tctgaaatgg cctatgaagc tgtggaactg acagctgcag aaatgcgtgg | 960 | |
| cactggagag gagtccaggg aaggtggcca gaaaagcttt ctatatagcg aattatccaa | 1020 | |
| caagagcaaa agtggagaca acagatgtcc cagagagag agcaaagaat ttgcagattc | 1080 | |
| catcagcaag gggctcatgg tttatgcaaa tcaggtggca tctgacatga tggtctctct | 1140 | |
| catgaagacc ttgaaagtgc acagctctgg gaagccaatt ccagcatctg tggtcctgaa | 1200 | |
| gagggtgttg ctaaggcaca ccaaggagat tgtgtccgat ttgattgatt cttgcatgaa | 1260 | |
| gaacctgcat aatattactg gggtcctgat gactgactca gactttgtct cagctgtcaa | 1320 | |
| gagaaatctg ttcaaccagt ggaaacaaaa tgctacagac atcatggagg ccatgctgaa | 1380 | |
| gcgcttggtc agtgccctta taggtgagga aaggagact aagtctcaga gtctgtcata | 1440 | |
| tgcatcttta aaagctgggt cccatgatcc caaatgcagg aatcagagtc ttgaattctc | 1500 | |
| caccatgaaa gctgaaatga agagaggga caaaggcaaa atgaaatcag acccatgcaa | 1560 | |
| gtcactgact agtgctgaga agtcggtga acacattctc aaagagggcc taaccatctg | 1620 | |
| gaaccaaaag caaggaaact catgcaaggt ggctaccaaa gcatgcagca ataaagatga | 1680 | |
| gaaaggagaa aagatcaatg cttccacaga ttcactggcc aaggacctga ttgtctctgc | 1740 | |
| ccttaagctg atccagtacc atctgaccca gcagactaag ggcaaagata catgtgaaga | 1800 | |
| agactgtcct ggttccacca tgggctatat ggctcagagt actcaatatg aaaagtgtgg | 1860 | |
| aggtggccaa agtgccaaag cactttcagt gaaacaacta gaatctcaca gagcccctgg | 1920 | |
| accatccacc tgtcaaaagg agaaccaaca cctggactcc cagaaaatgg atatgtcaaa | 1980 | |
| catcgttcta atgctgattc agaaactgct taatgagaac cccttcaaat gtgaggatcc | 2040 | |
| atgcgaaggt gagaacaagt gttctgagcc cagggcaagc aaagcagctt ccatgtccaa | 2100 | |
| cagatctgac aaagcggaag aacaatgcca ggagcatcaa gaacttgact gtaccagtgg | 2160 | |
| gatgaagcaa gcgaacgggc aatttataga taaactagta gaatctgtga tgaagctctg | 2220 | |
| ccttatcatg gctaagtata gcaacgatgg ggcagcccttt gctgagttgg aagaacaagc | 2280 | |
| agcctcggca aataagccca atttcagggg caccagatgc attcacagtg gtgcaatgcc | 2340 | |
| acagaactat caagactctc ttggacatga agtaattgtc aataatcagt gctctacaaa | 2400 | |
| tagcttgcag aagcagctcc aggctgtcct gcagtggatt gcagcctccc agtttaacgt | 2460 | |
| gcccatgctc tacttcatgg gagataagga tggacaactg gaaaagcttc ctcaggtttc | 2520 | |
| agctaaagca gcagagaagg ggtacagtgt aggaggtctt cttcaagagg tcatgaagtt | 2580 | |
| tgccaaggaa cggcaaccag atgaagctgt gggaaaggtg gccaggaaac agttgctgga | 2640 | |
| ctggctgctc gctaacctgt gagctgatcc ttgactcctc ttcatcttag cccccctagc | 2700 | |
| agcattccat cccagccaga gcaccccac catcaggcca gtcaactgca caatacacaa | 2760 | |
| ctgtatttcc caatacactt gagcagttgc ctgtgaatgt aagaggtgtc aacaaactgg | 2820 | |
| gaaataaaat aaaaaaaaat aataaaaaaa aaaaaaaaa aaaaaa | 2867 | |

<210> SEQ ID NO 4
<211> LENGTH: 845
<212> TYPE: PRT
<213> ORGANISM: Homo sapiens

<400> SEQUENCE: 4

```
Met Ser Asp Asp Ile Asp Trp Leu Arg Ser His Arg Gly Val Cys Lys
1               5                   10                  15

Val Asp Leu Tyr Asn Pro Glu Gly Gln Asp Gln Asp Arg Lys Val
            20                  25                  30

Ile Cys Phe Val Asp Val Ser Thr Leu Asn Val Glu Asp Lys Asp Tyr
            35                  40                  45

Lys Asp Ala Ala Ser Ser Ser Glu Gly Asn Leu Asn Leu Gly Ser
        50                  55                  60

Leu Glu Glu Lys Glu Ile Ile Val Ile Lys Asp Thr Glu Lys Lys Asp
65                      70                  75                  80

Gln Ser Lys Thr Glu Gly Ser Val Cys Leu Phe Lys Gln Ala Pro Ser
                85                  90                  95

Asp Pro Val Ser Val Leu Asn Trp Leu Leu Ser Asp Leu Gln Lys Tyr
                100                 105                 110

Ala Leu Gly Phe Gln His Ala Leu Ser Pro Ser Thr Ser Thr Cys Lys
            115                 120                 125

His Lys Val Gly Asp Thr Glu Gly Glu Tyr His Arg Ala Ser Ser Glu
        130                 135                 140

Asn Cys Tyr Ser Val Tyr Ala Asp Gln Val Asn Ile Asp Tyr Leu Met
145                 150                 155                 160

Asn Arg Pro Gln Asn Leu Arg Leu Glu Met Thr Ala Ala Lys Asn Thr
                165                 170                 175

Asn Asn Asn Gln Ser Pro Ser Ala Pro Pro Ala Lys Pro Pro Ser Thr
            180                 185                 190

Gln Arg Ala Val Ile Ser Pro Asp Gly Glu Cys Ser Ile Asp Asp Leu
            195                 200                 205

Ser Phe Tyr Val Asn Arg Leu Ser Ser Leu Val Ile Gln Met Ala His
        210                 215                 220

Lys Glu Ile Lys Glu Lys Leu Glu Gly Lys Ser Lys Cys Leu His His
225                 230                 235                 240

Ser Ile Cys Pro Ser Pro Gly Asn Lys Glu Arg Ile Ser Pro Arg Thr
                245                 250                 255

Pro Ala Ser Lys Ile Ala Ser Glu Met Ala Tyr Glu Ala Val Glu Leu
            260                 265                 270

Thr Ala Ala Glu Met Arg Gly Thr Gly Glu Glu Ser Arg Glu Gly Gly
        275                 280                 285

Gln Lys Ser Phe Leu Tyr Ser Glu Leu Ser Asn Lys Ser Lys Ser Gly
    290                 295                 300

Asp Lys Gln Met Ser Gln Arg Glu Ser Lys Glu Phe Ala Asp Ser Ile
305                 310                 315                 320

Ser Lys Gly Leu Met Val Tyr Ala Asn Gln Val Ala Ser Asp Met Met
            325                 330                 335

Val Ser Leu Met Lys Thr Leu Lys Val His Ser Ser Gly Lys Pro Ile
        340                 345                 350

Pro Ala Ser Val Val Leu Lys Arg Val Leu Leu Arg His Thr Lys Glu
            355                 360                 365

Ile Val Ser Asp Leu Ile Asp Ser Cys Met Lys Asn Leu His Asn Ile
        370                 375                 380

Thr Gly Val Leu Met Thr Asp Ser Asp Phe Val Ser Ala Val Lys Arg
385                 390                 395                 400

Asn Leu Phe Asn Gln Trp Lys Gln Asn Ala Thr Asp Ile Met Glu Ala
                405                 410                 415
```

```
Met Leu Lys Arg Leu Val Ser Ala Leu Ile Gly Glu Glu Lys Glu Thr
                420                 425                 430

Lys Ser Gln Ser Leu Ser Tyr Ala Ser Leu Lys Ala Gly Ser His Asp
            435                 440                 445

Pro Lys Cys Arg Asn Gln Ser Leu Glu Phe Ser Thr Met Lys Ala Glu
    450                 455                 460

Met Lys Glu Arg Asp Lys Gly Lys Met Lys Ser Asp Pro Cys Lys Ser
465                 470                 475                 480

Leu Thr Ser Ala Glu Lys Val Gly Glu His Ile Leu Lys Glu Gly Leu
                485                 490                 495

Thr Ile Trp Asn Gln Lys Gln Gly Asn Ser Cys Lys Val Ala Thr Lys
            500                 505                 510

Ala Cys Ser Asn Lys Asp Glu Lys Gly Glu Lys Ile Asn Ala Ser Thr
        515                 520                 525

Asp Ser Leu Ala Lys Asp Leu Ile Val Ser Ala Leu Lys Leu Ile Gln
    530                 535                 540

Tyr His Leu Thr Gln Gln Thr Lys Gly Lys Asp Thr Cys Glu Glu Asp
545                 550                 555                 560

Cys Pro Gly Ser Thr Met Gly Tyr Met Ala Gln Ser Thr Gln Tyr Glu
                565                 570                 575

Lys Cys Gly Gly Gly Gln Ser Ala Lys Ala Leu Ser Val Lys Gln Leu
            580                 585                 590

Glu Ser His Arg Ala Pro Gly Pro Ser Thr Cys Gln Lys Glu Asn Gln
        595                 600                 605

His Leu Asp Ser Gln Lys Met Asp Met Ser Asn Ile Val Leu Met Leu
    610                 615                 620

Ile Gln Lys Leu Leu Asn Glu Asn Pro Phe Lys Cys Glu Asp Pro Cys
625                 630                 635                 640

Glu Gly Glu Asn Lys Cys Ser Glu Pro Arg Ala Ser Lys Ala Ala Ser
                645                 650                 655

Met Ser Asn Arg Ser Asp Lys Ala Glu Glu Cys Gln Glu His Gln
            660                 665                 670

Glu Leu Asp Cys Thr Ser Gly Met Lys Gln Ala Asn Gly Gln Phe Ile
        675                 680                 685

Asp Lys Leu Val Glu Ser Val Met Lys Leu Cys Leu Ile Met Ala Lys
    690                 695                 700

Tyr Ser Asn Asp Gly Ala Ala Leu Ala Glu Leu Glu Gln Ala Ala
705                 710                 715                 720

Ser Ala Asn Lys Pro Asn Phe Arg Gly Thr Arg Cys Ile His Ser Gly
                725                 730                 735

Ala Met Pro Gln Asn Tyr Gln Asp Ser Leu Gly His Glu Val Ile Val
            740                 745                 750

Asn Asn Gln Cys Ser Thr Asn Ser Leu Gln Lys Gln Leu Gln Ala Val
        755                 760                 765

Leu Gln Trp Ile Ala Ala Ser Gln Phe Asn Val Pro Met Leu Tyr Phe
    770                 775                 780

Met Gly Asp Lys Asp Gly Gln Leu Glu Lys Leu Pro Gln Val Ser Ala
785                 790                 795                 800

Lys Ala Ala Glu Lys Gly Tyr Ser Val Gly Leu Leu Gln Glu Val
                805                 810                 815

Met Lys Phe Ala Lys Glu Arg Gln Pro Asp Glu Ala Val Gly Lys Val
            820                 825                 830

Ala Arg Lys Gln Leu Leu Asp Trp Leu Leu Ala Asn Leu
```

-continued

```
<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tcctacatga tggcgtactc tg                                          22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
aagttgcctt ctgagctgga ac                                          22

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
gggtgtgtgc aaggtagatc tct                                         23

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
cacatcgaca aagcatatca ctttc                                       25

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gccataccac cctgaacg                                               18

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
agcctacagc acccggtatt                                             20
```